(12) United States Patent
Okada

(10) Patent No.: US 9,791,793 B2
(45) Date of Patent: Oct. 17, 2017

(54) ELECTROPHOTOGRAPHIC PHOTOSENSITIVE MEMBER

(71) Applicant: KYOCERA Document Solutions Inc., Osaka (JP)

(72) Inventor: Hideki Okada, Osaka (JP)

(73) Assignee: KYOCERA Document Solutions Inc., Osaka (JP)

( * ) Notice: Subject to any disclaimer, the term of this patent is extended or adjusted under 35 U.S.C. 154(b) by 0 days.

(21) Appl. No.: 15/216,070

(22) Filed: Jul. 21, 2016

(65) Prior Publication Data

US 2017/0031253 A1 Feb. 2, 2017

(30) Foreign Application Priority Data

Jul. 30, 2015 (JP) ................................. 2015-150473

(51) Int. Cl.
| | | |
|---|---|---|
| *G03G 5/06* | (2006.01) | |
| *C07C 211/54* | (2006.01) | |
| *C07C 217/80* | (2006.01) | |

(52) U.S. Cl.
CPC .......... *G03G 5/0614* (2013.01); *C07C 211/54* (2013.01); *C07C 217/80* (2013.01); *G03G 5/0609* (2013.01); *G03G 5/0696* (2013.01)

(58) Field of Classification Search
CPC ... G03G 5/0614; G03G 5/0609; C07C 211/54
USPC ................................................. 430/58.85, 73
See application file for complete search history.

(56) References Cited

U.S. PATENT DOCUMENTS

| | | | |
|---|---|---|---|
| 7,083,862 B2 * | 8/2006 | Burn ..................... | C07C 211/54 313/504 |
| 8,349,529 B2 * | 1/2013 | Shimoyama ......... | G03G 5/0614 399/159 |
| 2004/0058257 A1 * | 3/2004 | Azuma ................. | G03G 5/0675 430/56 |

FOREIGN PATENT DOCUMENTS

| | | | |
|---|---|---|---|
| JP | 01-155356 | * | 6/1989 |
| JP | 05-092936 A | * | 4/1993 |
| JP | 2013-056905 A | | 3/2013 |

OTHER PUBLICATIONS

Japanese Patent Office J-PlatPat machine assisted English-language translation of JP 05-092936 A (pub. Apr. 1993).*
Japanese Patent Office J-PlatPat machine assisted English-language translation of JP 01-155356 (pub. Jun. 1989).*
Sun et al., Science in China Series B: Chemistry, (2008), vol. 51(1), pp. 92-96.*

* cited by examiner

*Primary Examiner* — Janis L Dote
(74) *Attorney, Agent, or Firm* — Studebaker & Brackett PC

(57) ABSTRACT

A triphenylamine derivative is represented by general formula (1). In the general formula (1): $R_1$, $R_2$, $R_3$, $R_4$, $R_5$, $R_6$, $R_7$, $R_8$, $R_9$, and $R_{10}$ each represent, independently of one another, a hydrogen atom, an optionally substituted alkyl group having a carbon number of at least 1 and no greater than 6, an optionally substituted alkoxy group having a carbon number of at least 1 and no greater than 6, an optionally substituted alkenyl group having a carbon number of at least 2 and no greater than 6, or an optionally substituted aryl group having a carbon number of at least 6 and no greater than 14; m represents an integer of at least 1 and no greater than 3; and n represents an integer of at least 0 and no greater than 2.

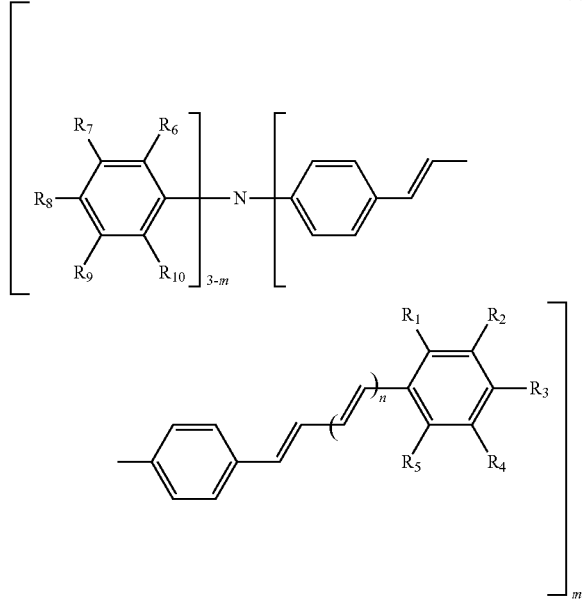

3 Claims, 5 Drawing Sheets

ELECTROPHOTOGRAPHIC PHOTOSENSITIVE MEMBER

INCORPORATION BY REFERENCE

The present application claims priority under 35 U.S.C. §119 to Japanese Patent Application No. 2015-150473, filed on Jul. 30, 2015. The contents of this application are incorporated herein by reference in their entirety.

BACKGROUND

The present disclosure relates to triphenylamine derivatives and electrophotographic photosensitive members.

An electrophotographic photosensitive member is adopted in an electrographic image forming apparatus. The electrophotographic photosensitive member includes a photosensitive layer. The electrophotographic photosensitive member may be a multi-layer electrophotographic photosensitive member or a single-layer electrophotographic photosensitive member, for example. The photosensitive layer of the multi-layer electrophotographic photosensitive member includes a charge generating layer having a function of charge generation and a charge transport layer having a function of charge transport. The photosensitive layer of the single-layer electrophotographic photosensitive member includes a single-layer type photosensitive layer having functions of charge generation and transport.

An example electrophotographic photosensitive member contains a charge transport material. The charge transport material may be for example a tris(4-styrylphenyl)amine derivative represented by chemical formula (HT-A) or (HT-B).

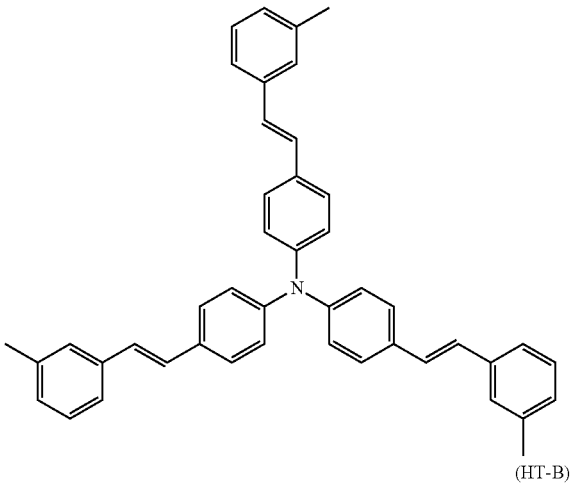

(HT-A)

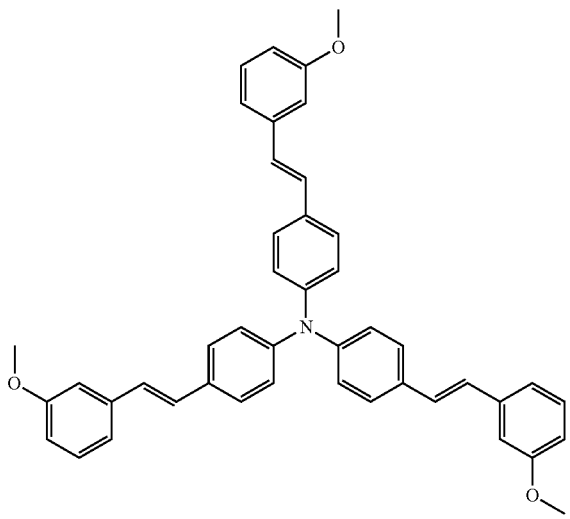

(HT-B)

SUMMARY

A triphenylamine derivative according to the present disclosure is represented by the following general formula (1).

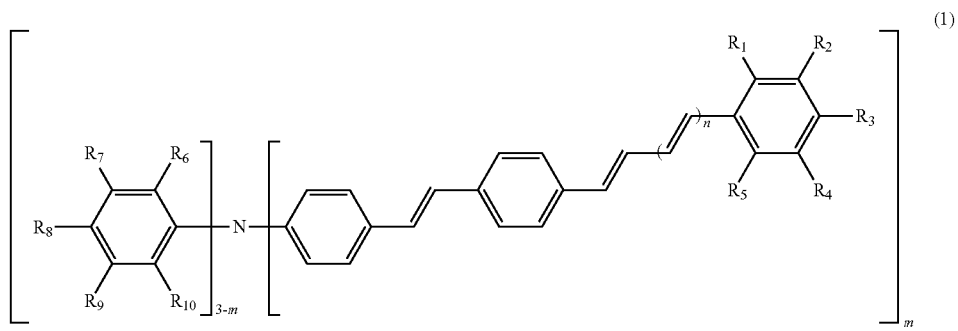

(1)

In general formula (1), $R_1$, $R_2$, $R_3$, $R_4$, $R_5$, $R_6$, $R_7$, $R_8$, $R_9$, and $R_{10}$ each represent, independently of one another, a hydrogen atom, an optionally substituted alkyl group having a carbon number of at least 1 and no greater than 6, an optionally substituted alkoxy group having a carbon number of at least 1 and no greater than 6, an optionally substituted alkenyl group having a carbon number of at least 2 and no greater than 6, or an optionally substituted aryl group having a carbon number of at least 6 and no greater than 14. Further, m represents an integer of at least 1 and no greater than 3 and n represents an integer of at least 0 and no greater than 2.

An electrophotographic photosensitive member according to the present disclosure includes a conductive substrate and a photosensitive layer. The photosensitive layer contains at least a charge generating material and the above triphenylamine derivative as a hole transport material.

DETAILED DESCRIPTION

Figure 1:
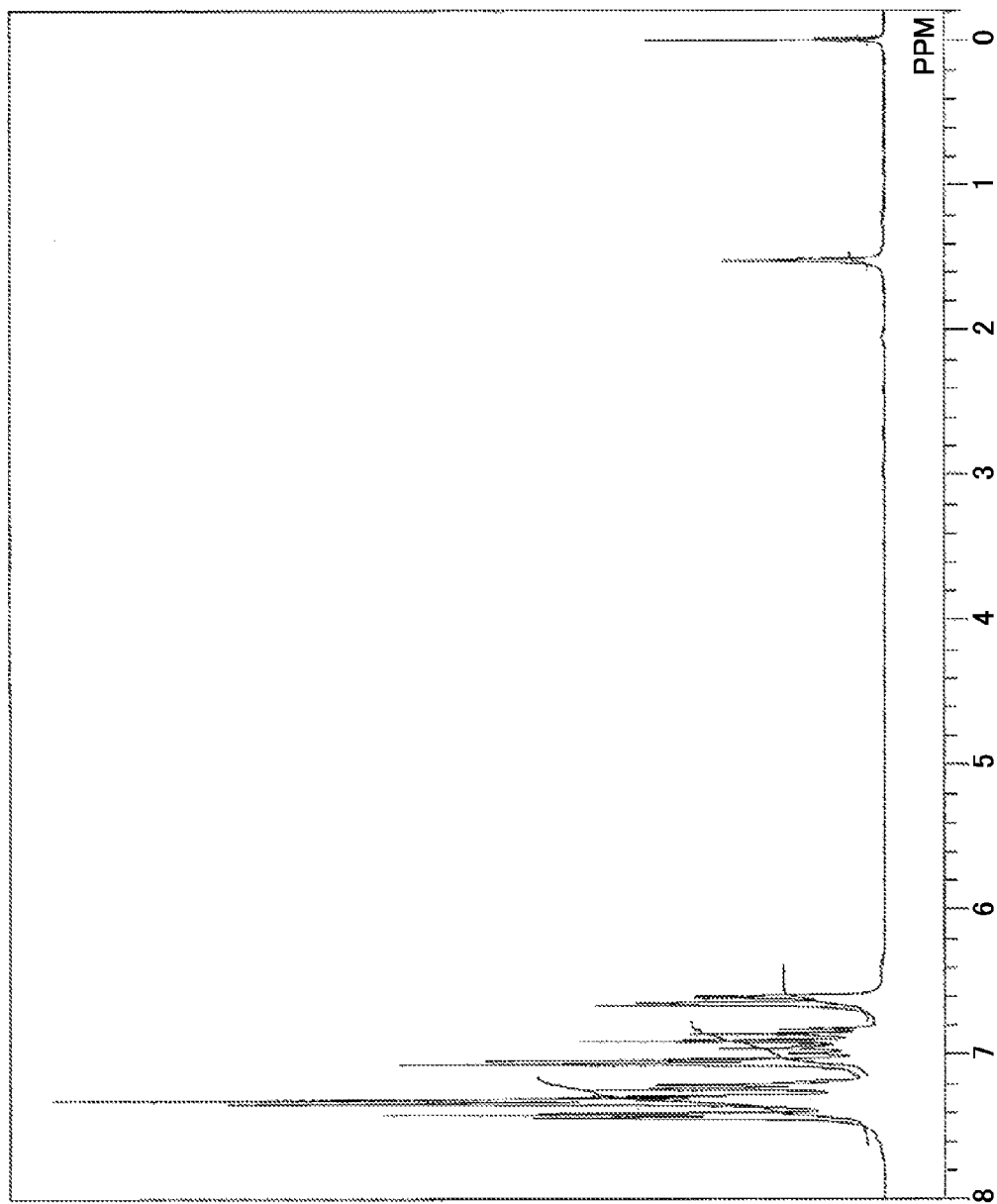
FIG. 1 shows a $^1$H-NMR spectrum of a triphenylamine derivative represented by chemical formula (HT-1) according to a first embodiment of the present disclosure.

The following describes embodiments of the present disclosure in detail. However, the present disclosure is in no way limited to the following embodiments. Appropriate alterations of the present disclosure may be made in practice within the intended scope of the present disclosure. Although description is omitted in some places in order to avoid repetition, such omission does not limit the essence of the present disclosure.

In the present description, the term "-based" may be appended to the name of a chemical compound in order to form a generic name encompassing both the chemical compound itself and derivatives thereof. Also, when the term "-based" is appended to the name of a chemical compound used in the name of a polymer, the term indicates that a repeating unit of the polymer originates from the chemical compound or a derivative thereof. Further, compounds represented by general formulas or chemical formulas (2)-(13), (2a), (3a), (4a)-(4c), (5a)-(5c), (7a), (8a), (8b), (9a), (11a), (11b), (12b), (12c), (13b), and (13c) may be referred to as compound 2-13, 2a, 3a, 4a-4c, 5a-5c, 7a, 8a, 8b, 9a, 11a, 11b, 12b, 12c, 13b, and 13c, respectively. Reactions represented by reaction formulas (R-1)-(R-22) may be referred to as Reactions R-1-R-22, respectively.

Unless otherwise stated, a halogen atom, an alkyl group having a carbon number of at least 1 and no greater than 6, an alkoxy group having a carbon number of at least 1 and no greater than 6, an alkenyl group having a carbon number of at least 2 and no greater than 6, an aryl group having a carbon number of at least 6 and no greater than 14 are those described below.

Examples of halogen atoms include fluorine (a fluoro group), chlorine (a chloro group), or bromine (a bromo group).

The alkyl group having a carbon number of at least 1 and no greater than 6 is a straight- or branched-chain unsubstituted alkyl group having a carbon number of at least 1 and no greater than 6. Examples of alkyl groups having a carbon number of at least 1 and no greater than 6 include a methyl group, an ethyl group, a propyl group, an isopropyl group, an n-butyl group, an s-butyl group, a t-butyl group, a pentyl group, an isopentyl group, a neopentyl group, and a hexyl group.

The alkoxy group having a carbon number of at least 1 and no greater than 6 is a straight- or branched-chain unsubstituted alkoxy group having a carbon number of at least 1 and no greater than 6. Examples of alkoxy groups having a carbon number of at least 1 and no greater than 6 include a methoxy group, an ethoxy group, an n-propoxy group, an isopropoxy group, an n-butoxy group, an s-butoxy group, a t-butoxy group, a pentyloxy group, an isopentyloxy group, a neopentyloxy group, and a hexyloxy group.

The alkenyl group having a carbon number of at least 2 and no greater than 6 is a straight- or branched-chain unsubstituted alkenyl group having a carbon number of at least 2 and no greater than 6. Alkenyl groups having a carbon number of at least 2 and no greater than 6 each have at least one and no greater than three double bonds. Examples of alkenyl groups having a carbon number of at least 2 and no greater than 6 include a vinyl group, a propenyl group, a butenyl group, a butadienyl group, a pentenyl group, a pentadienyl group, a hexenyl group, a hexadienyl group, and a hexatrienyl group.

The aryl group having a carbon number of at least 6 and no greater than 14 is an unsubstituted aromatic monocyclic hydrocarbon group having a carbon number of at least 6 and no greater than 14, an unsaturated condensed bicyclic aromatic hydrocarbon group having a carbon number of at least 6 and no greater than 14, or an unsubstituted condensed tricyclic aromatic hydrocarbon group having a carbon number of at least 6 and no greater than 14. Examples of aryl groups having a carbon number of at least 6 and no greater than 14 include a phenyl group, a naphthyl group, an anthryl group, and a phenanthryl group.

First Embodiment: Triphenylamine Derivative

A first embodiment of the present disclosure is directed to a triphenylamine derivative. The triphenylamine derivative in the present embodiment is represented by the following general formula (1).

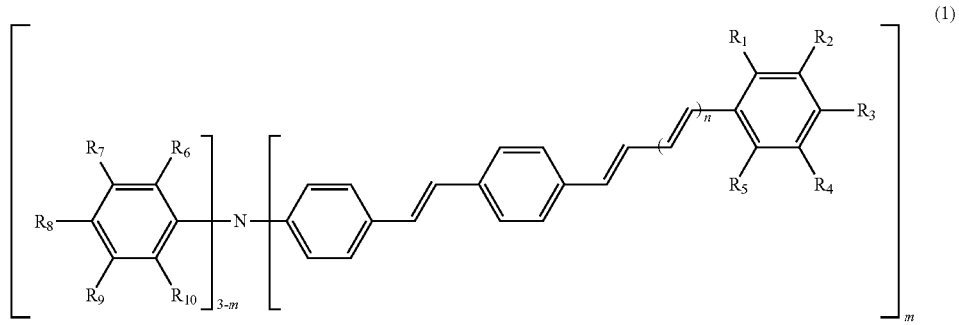

In general formula (1), $R_1$, $R_2$, $R_3$, $R_4$, $R_5$, $R_6$, $R_7$, $R_8$, $R_9$, and $R_{10}$ each represent, independently of one another, a hydrogen atom, an optionally substituted alkyl group having a carbon number of at least 1 and no greater than 6, an optionally substituted alkoxy group having a carbon number of at least 1 and no greater than 6, an optionally substituted alkenyl group having a carbon number of at least 2 and no greater than 6, or an optionally substituted aryl group having a carbon number of at least 6 and no greater than 14. Also, m represents an integer of at least 1 and no greater than 3 and n represents an integer of at least 0 and no greater than 2.

The triphenylamine derivative represented by general formula (1) (also referred to below as a triphenylamine derivative 1), when contained in a photosensitive layer of the electrophotographic photosensitive member, can improve electric properties of an electrophotographic photosensitive member. The reason thereof is thought to be as follows.

The triphenylamine derivative 1 has a nitrogen atom. At least one and no greater than three groups (conjugated groups) including a phenyl group having $R_1$-$R_5$ are bonded to the nitrogen atom. In a configuration having conjugated groups as above, the triphenylamine derivative 1 has an appropriately large molecular structure. In the above configuration, a distance (hopping distance) between the π electron cloud of a molecule of the triphenylamine derivative 1 and the π electron cloud of another adjacent molecule of the triphenylamine derivative 1 that are present in a photosensitive layer tends to be small. It is thought that as a result, hole mobility between molecules of the triphenylamine derivative 1 is improved, and thus electric properties of the electrophotographic photosensitive member is improved.

The alkyl group having a carbon number of at least 1 and no greater than 6 and represented by $R_1$-$R_{10}$ in general formula (1) is preferably an alkyl group having a carbon number of at least 1 and no greater than 3, and more preferably a methyl group. The alkyl group having a carbon number of at least 1 and no greater than 6 and represented by $R_1$-$R_{10}$ in general formula (1) may have a substituent. Examples of substituents that the alkyl group having a carbon number of at least 1 and no greater than 6 may have include a halogen atom, alkoxy groups having a carbon number of at least 1 and no greater than 6, and aryl groups having a carbon number of least 6 and no greater than 14. Although no particular limitations are placed on the number of substituents of the alkyl group, the alkyl group preferably has no greater than three substituents.

The alkoxy group having a carbon number of at least 1 and no greater than 6 and represented by $R_1$-$R_{10}$ in general formula (1) is preferably an alkoxy group having a carbon number of at least 1 and no greater than 3. The alkoxy group having a carbon number of at least 1 and no greater than 6 and represented by $R_1$-$R_{10}$ in general formula (1) may have a substituent. Examples of substituents that the alkoxy group having a carbon number of at least 1 and no greater than 6 may have include a halogen atom, alkoxy groups having a carbon number of at least 1 and no greater than 6, and aryl groups having a carbon number of least 6 and no greater than 14. Although no particular limitations are placed on the number of substituents of the alkoxy group, the alkoxy group preferably has no greater than three substituents.

The alkenyl group having a carbon number of at least 2 and no greater than 6 and represented by $R_1$-$R_{10}$ in general formula (1) is preferably an alkenyl group having a carbon number of at least 2 and no greater than 4, and more preferably a vinyl group or a butadienyl group. The alkenyl group having a carbon number of at least 2 and no greater than 6 and represented by $R_1$-$R_{10}$ in general formula (1) may have a substituent.

Examples of substituents that the alkenyl group having a carbon number of at least 2 and no greater than 6 may have include a halogen atom, alkoxy groups having a carbon number of at least 1 and no greater than 6, and optionally substituted aryl groups having a carbon number of least 6 and no greater than 14. An optionally substituted aryl group having a carbon number of at least 6 and no greater than 14 is preferable as a substituent of the alkenyl group having a carbon number of at least 2 and no greater than 6. Examples of alkenyl group having a carbon number of at least 2 and no greater than 6 that has an optionally substituted aryl group having a carbon number of at least 6 and no greater than 14 include a group represented by the following general formula.

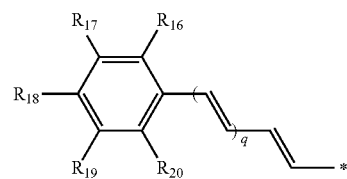

In the above general formula, $R_{16}$, $R_{17}$, $R_{18}$, $R_{19}$, and $R_{20}$ each represent, independently of one another, a hydrogen atom, an alkyl group having a carbon number of at least 1 and no greater than 6, an alkoxy group having a carbon number of at least 1 and no greater than 6, or an aryl group having a carbon number of at least 6 and no greater than 14. Also, q represents an integer of at least 0 and no greater than 2 and * represents a bonding site.

The aryl group having a carbon number of at least 6 and no greater than 14 and represented by $R_1$-$R_{10}$ in general formula (1) is preferably an aromatic monocyclic hydrocarbon group having a carbon number of at least 6 and no greater than 14, and more preferably a phenyl group. The aryl group having a carbon number of at least 6 and no greater than 14 and represented by $R_1$-$R_{10}$ in general formula (1) may have a substituent. Examples of substituents that the aryl group having a carbon number of at least 6 and no greater than 14 may have include a halogen atom, alkyl groups having a carbon number of at least 1 and no greater than 6, alkoxy groups having a carbon number of at least 1 and no greater than 6, and aryl groups having a carbon number of at least 6 and no greater than 14. Although no particular limitations are placed on the number of substituents of the aryl group, the aryl group preferably has no greater than three substituents and more preferably one substituent.

Examples of the triphenylamine derivative represented by general formula (1) include triphenylamine derivatives represented by general formulas (1-1) and (1-2).

The triphenylamine derivatives represented by general formulas (1-1) and (1-2) may be hereinafter referred to as triphenylamine derivatives 1-1 and 1-2, respectively.

In general formula (1-1), $R_{11}$, $R_{12}$, $R_{13}$, $R_{14}$, and $R_{15}$ preferably each represent, independently of one another, a hydrogen atom or an alkyl group having a carbon number of at least 1 and no greater than 6, more preferably a hydrogen atom or an alkyl group having a carbon number of at least 1 an no greater than 3, and further preferably a hydrogen atom or a methyl group. Moreover, $R_{11}$ preferably represents a hydrogen atom or an alkyl group having a carbon number of at least 1 and no greater than 6, more preferably a hydrogen atom or an alkyl group having a carbon number of at least 1 and no greater than 3, and further preferably a hydrogen atom or a methyl group. Yet, $R_{13}$ preferably represents an alkyl group having a carbon number of at least 1 and no greater than 6, more preferably an alkyl group having a carbon number of at least 1 and no greater than 3, and further preferably a methyl group. Particularly preferably, $R_{12}$, $R_{14}$, and $R_{15}$ each represent a hydrogen atom.

In general formula (1-2), $R_{16}$, $R_{17}$, $R_{18}$, $R_{19}$, and $R_{20}$ preferably each represent, independently of one another, a hydrogen atom or an alkyl group having a carbon number of at least 1 and no greater than 6, more preferably a hydrogen atom or an alkyl group having a carbon number of at least 1 and no greater than 3, and further preferably a hydrogen atom or a methyl group. Yet, $R_{16}$, $R_{17}$, $R_{19}$, and $R_{20}$

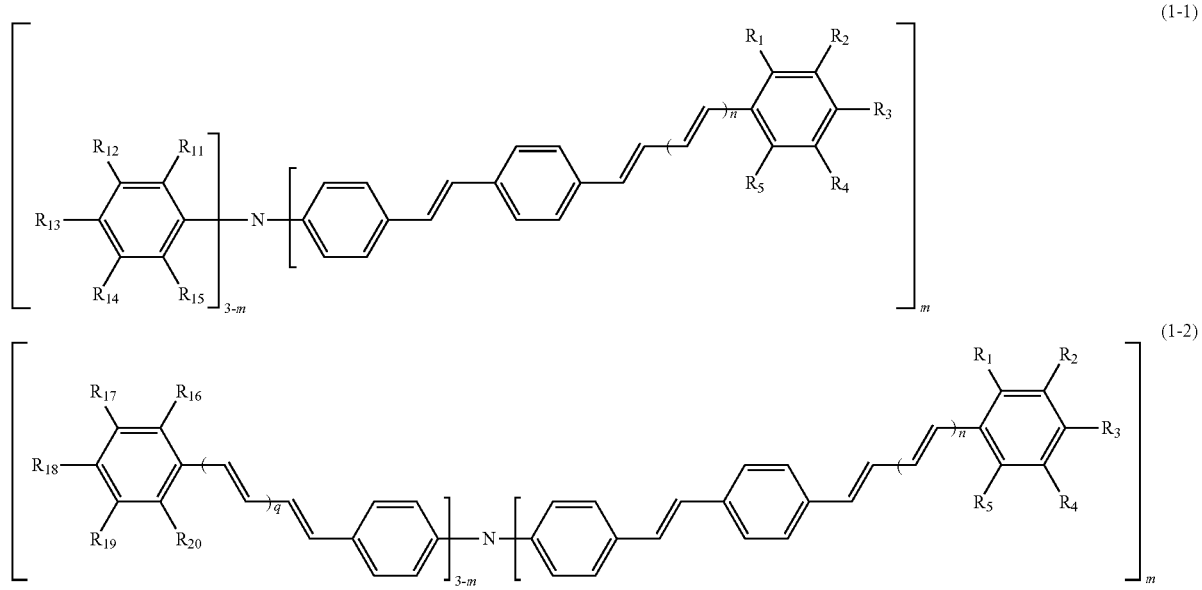

In general formulas (1-1) and (1-2), $R_1$, $R_2$, $R_3$, $R_4$, $R_5$, m, and n are equivalent to $R_1$, $R_2$, $R_3$, $R_4$, $R_5$, m, and n in general formula (1), respectively. Further, $R_{11}$, $R_{12}$, $R_{13}$, $R_{14}$, and $R_{15}$ each represent, independently of one another, a hydrogen atom, an alkyl group having a carbon number of at least 1 and no greater than 6, an alkoxy group having a carbon number of at least 1 and no greater than 6, or an aryl group having a carbon number of at least 6 and no greater than 14. Moreover, $R_{16}$, $R_{17}$, $R_{18}$, $R_{19}$, and $R_{20}$ each represent, independently of one another, a hydrogen atom, an alkyl group having a carbon number of at least 1 and no greater than 6, an alkoxy group having a carbon number of at least 1 and no greater than 6, or an aryl group having a carbon number of at least 6 and no greater than 14. Yet, q represents an integer of at least 0 and no greater than 2.

In general formulas (1-1) and (1-2), $R_1$, $R_2$, $R_3$, $R_4$, and $R_5$ preferably each represent a hydrogen atom.

preferably each represent a hydrogen atom. Still, $R_{18}$ preferably represents a hydrogen atom or an alkyl group having a carbon number of at least 1 and no greater than 6, more preferably a hydrogen atom or an alkyl group having a carbon number of at least 1 and no greater than 3, and further preferably a hydrogen atom or a methyl group.

In general formulas (1-1) and (1-2), m represents an integer of at least 1 and no greater than 3 and n represents an integer of at least 0 and no greater than 2. In order to improve electric properties of the electrophotographic photosensitive member, n preferably represents 0 or 1. Also, q represents an integer of at least 0 and no greater than 2. In order to improve electric properties of the electrophotographic photosensitive member, q preferably represents 0 or 1.

In order to improve electric properties of the electrophotographic photosensitive member, preferably, m represents 1 or 2 and q represents 1 in general formula (1-2). In order to inhibit crystallization in the photosensitive layer in addition to improvement of electric properties of the electrophotographic photosensitive member, further preferably, m represents 2 and q represents 1.

Another preferable example of the triphenylamine derivative to improve electric properties of the electrophotographic photosensitive member is a triphenylamine derivative represented by general formula (1-2) in which m represents 3 and n represents 1.

In order to improve electric properties of the electrophotographic photosensitive member, a triphenylamine derivative represented by general formula (1-2) is preferable among the triphenylamine derivatives represented by general formulas (1-1) and (1-2) that are examples of the triphenylamine derivative 1.

Specific examples of the triphenylamine derivative 1 include triphenylamine derivatives represented by chemical formulas (HT-1)-(HT-10) shown below. Hereinafter, the triphenylamine derivatives represented by chemical formulas (HT-1)-(HT-10) may be referred to as triphenylamine derivatives HT-1-HT-10, respectively. Compounds HT-5, HT-6, HT-7, and HT-8 are specific examples of the triphenylamine derivative 1-1 that is an example of the triphenylamine derivative 1. Compounds HT-1, HT-2, HT-3, HT-4, and HT-10 are specific examples of the triphenylamine derivative 1-2 that is an example of the triphenylamine derivative 1. The compound HT-9 is a specific example of the triphenylamine derivative 1-1 that is an example of the triphenylamine derivative 1 and also a specific example of the triphenylamine derivative 1-2 that is an example of the triphenylamine derivative 1.

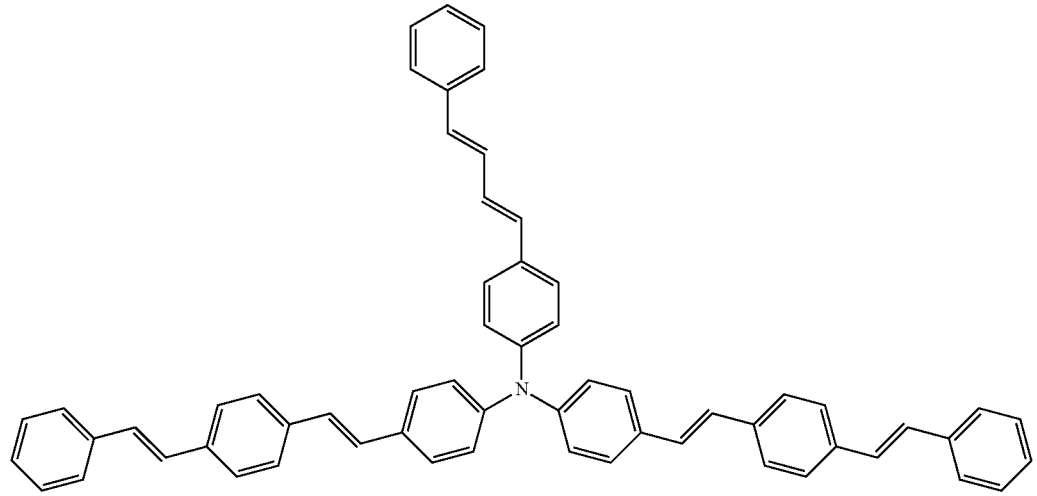

(HT-1)

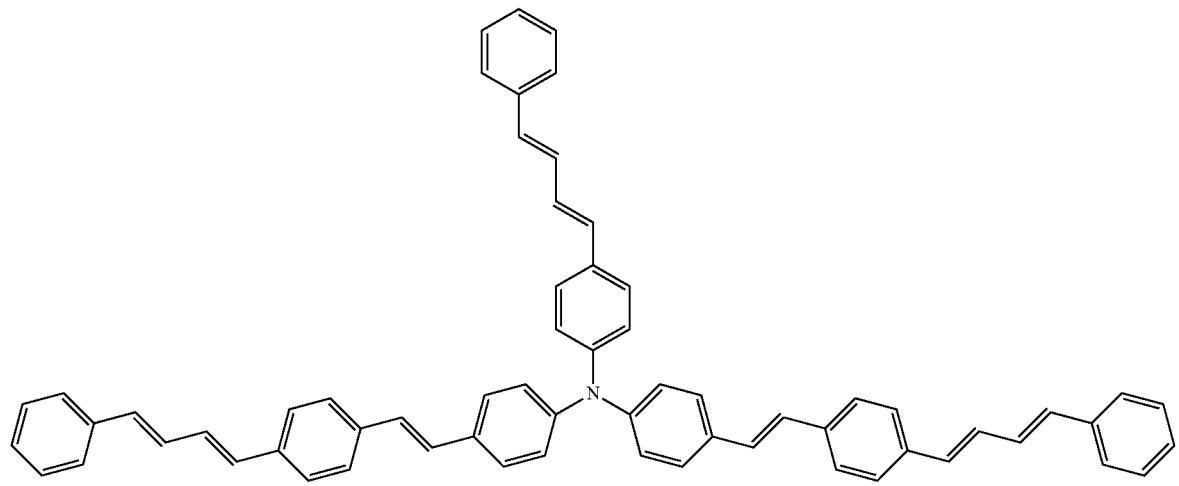

(HT-2)

-continued
(HT-3)
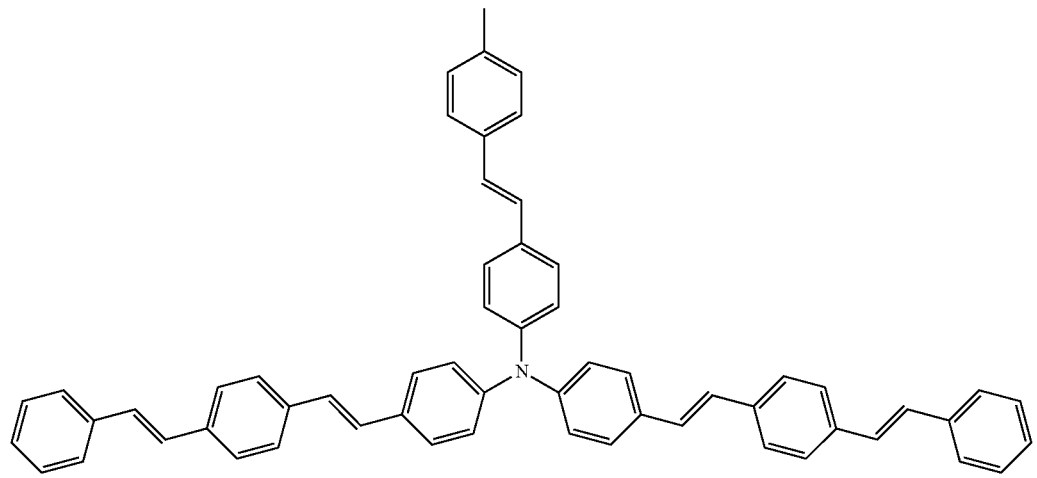
(HT-4)
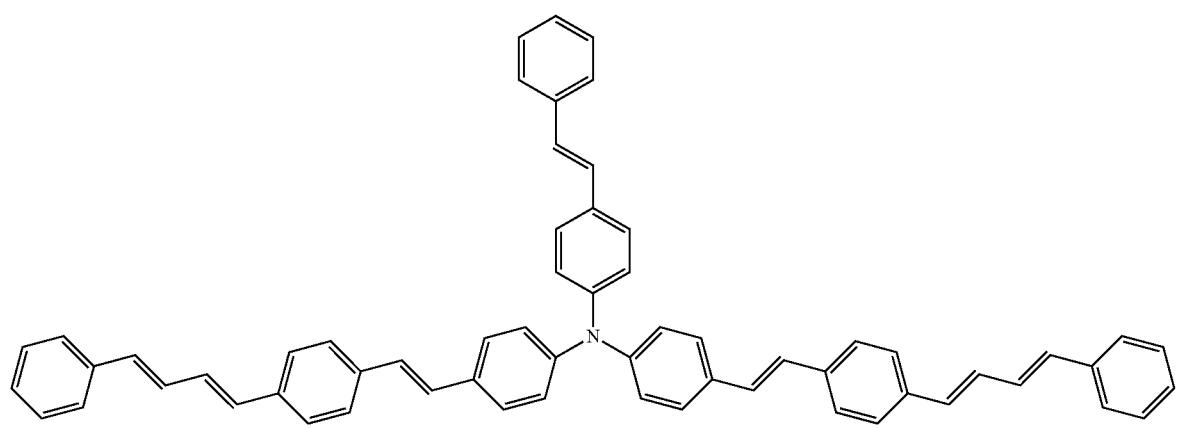
(HT-5)
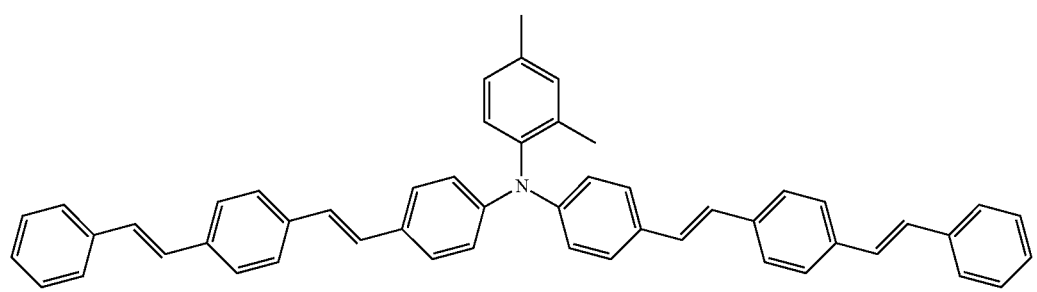
(HT-6)
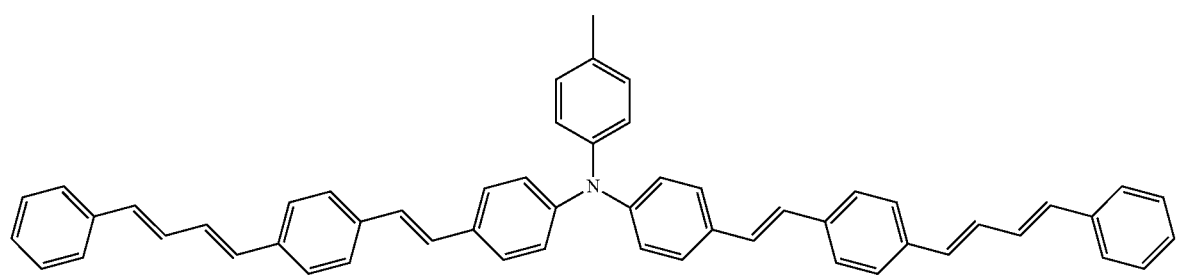

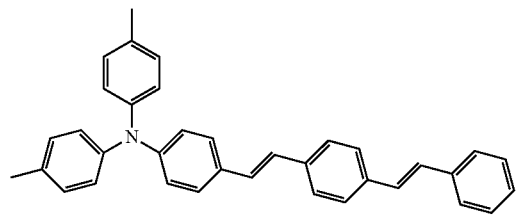
(HT-7)
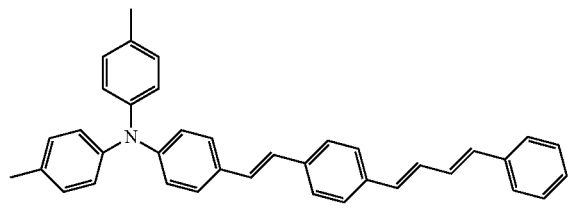
(HT-8)
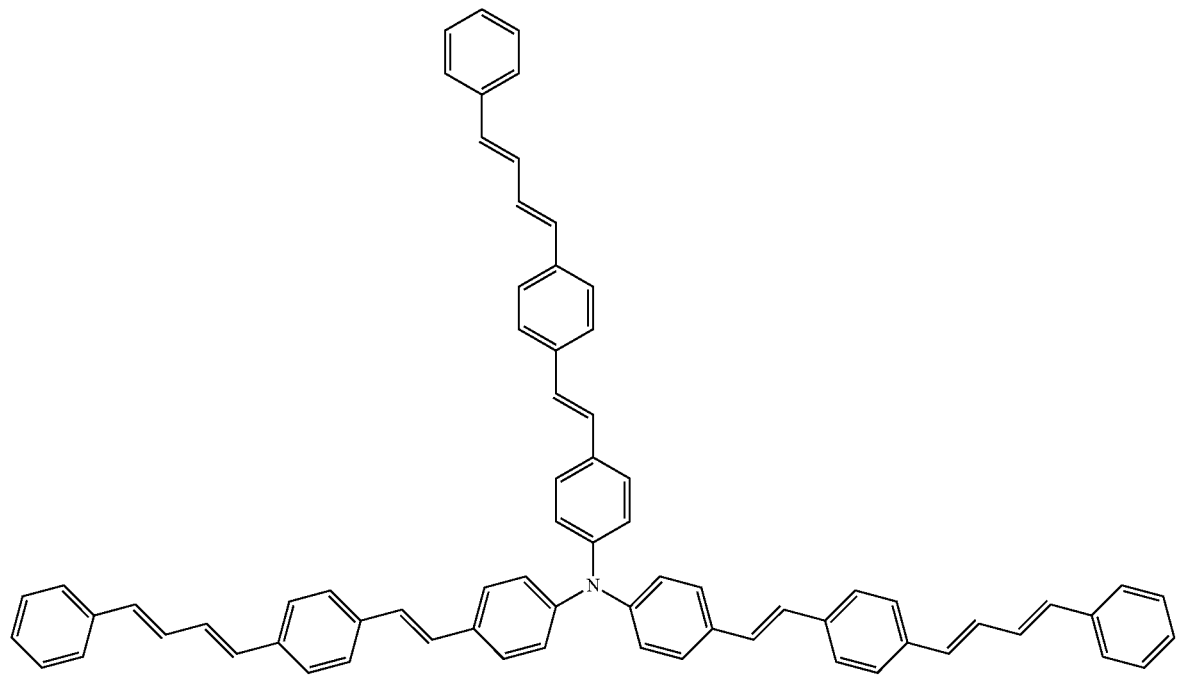
(HT-9)
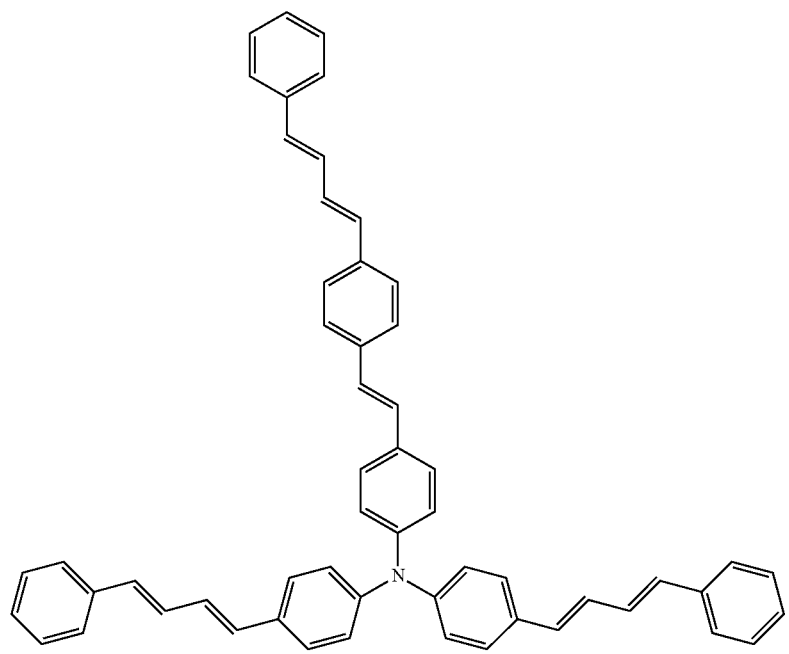
(HT-10)

A triphenylamine derivative 1 is produced according to for example the following method or a method conforming therewith. The following production method may involve an appropriate additional process depending on necessity thereof. An unnecessary process may be omitted according to properties of the triphenylamine derivative 1 to be produced.

A production method will be described by referring to triphenylamine derivatives represented by the following general formulas (1-3)-(1-7) among examples of the triphenylamine derivative 1. The triphenylamine derivatives represented by general formulas (1-3)-(1-7) may be hereinafter referred to as triphenylamine derivatives 1-3-1-7, respectively.

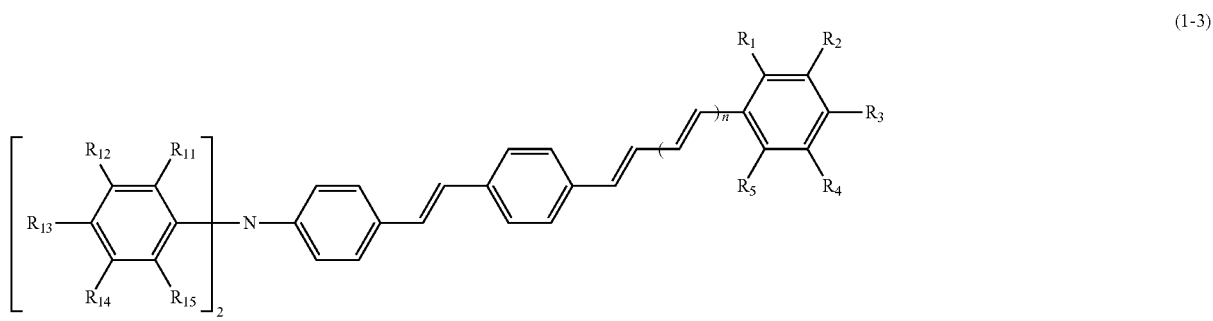

(1-3)

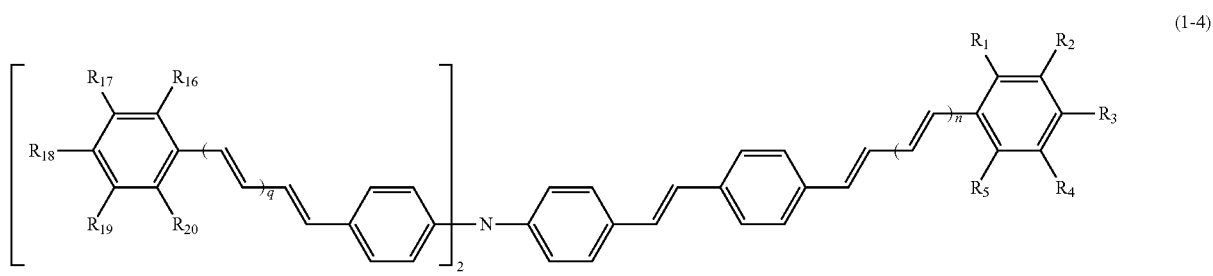

(1-4)

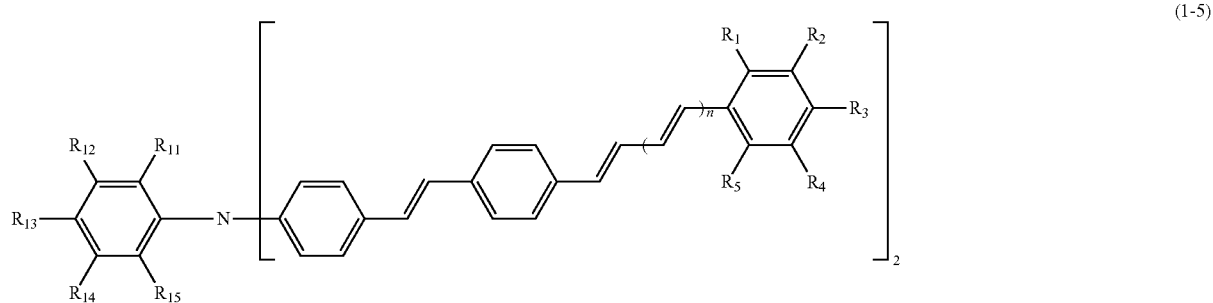

(1-5)

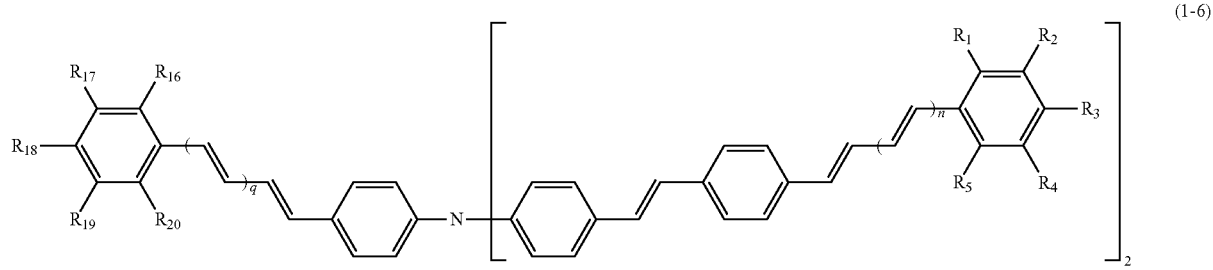

(1-6)

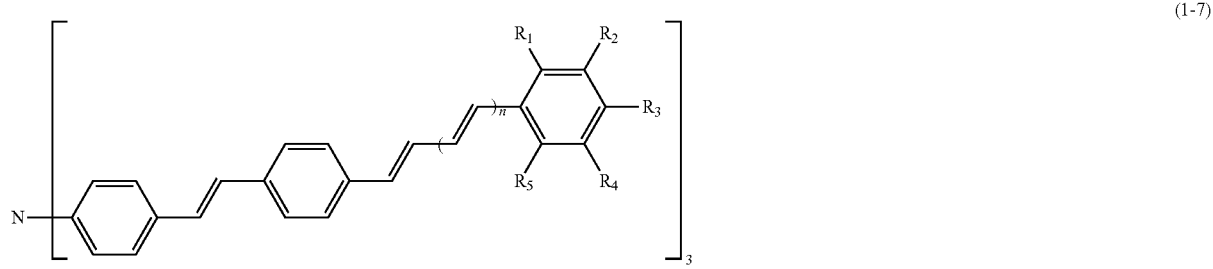

(1-7)

In general formulas (1-3)-(1-7), $R_1$, $R_2$, $R_3$, $R_4$, $R_5$, $R_{11}$, $R_{12}$, $R_{13}$, $R_{14}$, $R_{15}$, $R_{16}$, $R_{17}$, $R_{18}$, $R_{19}$, $R_{20}$, n, and q are equivalent to $R_1$, $R_2$, $R_3$, $R_4$, $R_5$, $R_{11}$, $R_{12}$, $R_{13}$, $R_{14}$, $R_{15}$, $R_{16}$, $R_{17}$, $R_{18}$, $R_{19}$, $R_{20}$, n, and q in general formulas (1-1) and (1-2), respectively.

(Synthesis of Compound 5)

First, a compound 5 is synthesized as a material used for synthesis of the triphenylamine derivatives 1-3-1-7. The compound 5 is synthesized through Reactions R-1 and R-2, for example.

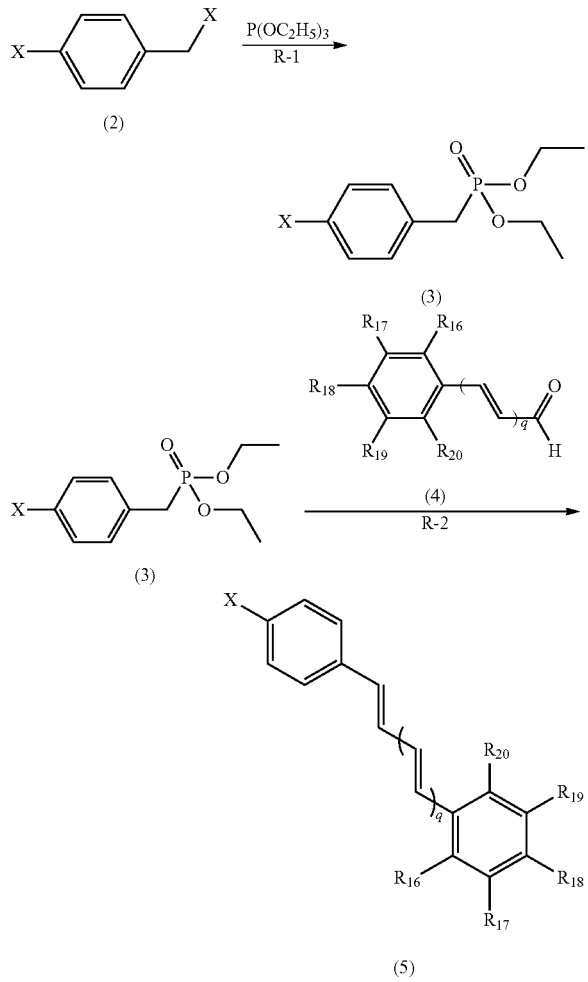

In reaction formulas (R-1) and (R-2), $R_{16}$, $R_{17}$, $R_{18}$, $R_{19}$, $R_{20}$, and q are equivalent to $R_{16}$, $R_{17}$, $R_{18}$, $R_{19}$, $R_{20}$, and q in general formula (1-2). Also, X represents a halogen atom.

(Reaction R-1)

In Reaction R-1, a compound 2 (1 chemical equivalent) is caused to react with triethyl phosphite (1 chemical equivalent) to yield a compound 3 (1 chemical equivalent).

In Reaction R-1, at least 1 mole and no greater than 2.5 moles of triethyl phosphite is preferably added relative to 1 mole of the compound 2. In a situation in which the number of moles of triethyl phosphite is too small relative to the number of moles of the compound 2, the percentage yield of the compound 3 may decrease. By contrast, in a situation in which the number of moles of triethyl phosphite is too large relative to the number of moles of the compound 2, unreacted triethyl phosphite may remain after reaction to make it difficult to purify the compound 3.

Reaction R-1 is preferably carried out at a reaction temperature of at least 160° C. and no greater than 200° C. and preferably has a reaction time of at least 2 hours and no greater than 10 hours.

(Reaction R-2)

In Reaction R-2, the compound 3 (1 chemical equivalent) is caused to react with a compound 4 (1 chemical equivalent) to yield the compound 5 (1 chemical equivalent). Reaction R-2 is a Wittig reaction.

In Reaction R-2, preferably, at least 1 mole and no greater than 2.5 moles of the compound 4 is added relative to 1 mole of the compound 3. In a situation in which the number of moles of the compound 4 is too small relative to the number of moles of the compound 3, the percentage yield of the compound 5 may decrease. By contrast, in a situation in which the number of moles of the compound 4 is too large relative to the number of moles of the compound 3, unreacted compound 4 may remain after reaction to make it difficult to purify the compound 5.

Reaction R-2 may be carried out under the presence of a base. Examples of bases that may be used include sodium alkoxides (specifically, sodium methoxide, or sodium ethoxide), metal hydrides (specifically, sodium hydride, or potassium hydride), and metal salts (specifically, n-butyl lithium). Any one of the above bases may be used or a combination of any two or more of the above bases may be used. An additive amount of the base is preferably at least 1 mole and no greater than 2 moles relative to 1 mole of the compound 3. In a situation in which the additive amount of the base is too small, reactivity may decrease. By contrast, in a situation in which the additive amount of the base is too large, reaction may be difficult to control.

Reaction R-2 may be carried out under the presence of a solvent. Examples of solvents that may be used include ethers (specifically, tetrahydrofuran, diethyl ether, or dioxane), halogenated hydrocarbons (specifically, methylene chloride, chloroform, or dichloroethane), and aromatic hydrocarbons (specifically, benzene or toluene).

Reaction R-2 is preferably carried out at a reaction temperature of at least 0° C. and no greater than 50° C. and preferably has a reaction time of at least 2 hours and no greater than 24 hours.

(Synthesis of Compound 8)

Subsequently, a compound 8 is synthesized as a material used for synthesis of the triphenylamine derivatives 1-3 to 1-7. The compound 8 is synthesized through Reactions R-3-R-5, for example.

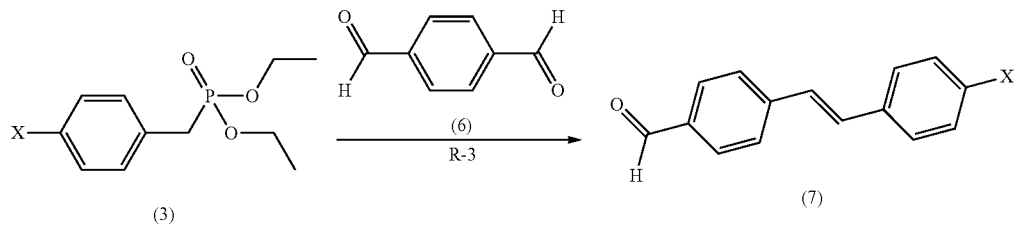

-continued

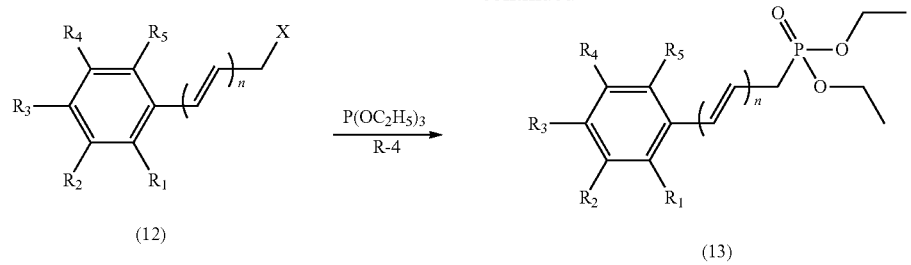

(12) → (13)

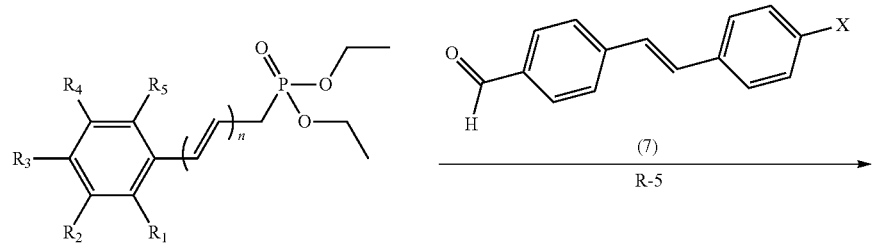

(13)

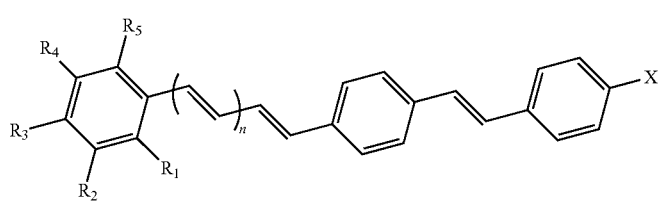

(8)

In reaction formulas (R-3)-(R-5), $R_1$, $R_2$, $R_3$, $R_4$, $R_5$, and n are equivalent to $R_1$, $R_2$, $R_3$, $R_4$, $R_5$, and n in general formula (1-1), respectively. Also, X represents a halogen atom.

(Reaction R-3)

In Reaction R-3, the compound 3 (1 chemical equivalent) is caused to react with a compound 6 (1 chemical equivalent) to yield a compound 7 (1 chemical equivalent). Reaction R-3 is a Wittig reaction. Note that the compound 3 can be yielded through Reaction R-1.

In Reaction R-3, preferably, at least 1 mole and no greater than 10 moles of the compound 6 is added relative to 1 mole of the compound 3. In a situation in which the number of moles of the compound 6 is too small relative to the number of moles of the compound 3, the percentage yield of the compound 7 may decrease. By contrast, in a situation in which the number of moles of the compound 6 is too large relative to the number of moles of the compound 3, unreacted compound 6 may remain after reaction to make it difficult to purify the compound 7.

Reaction R-3 may be carried out under the presence of a base. Examples of the base used in Reaction R-3 include the same bases as those listed as examples of the base used in Reaction R-2, for example. Any one of the above bases may be used or a combination of any two or more of the above base may be used. An additive amount of the base is preferably at least 1 mole and no greater than 2 moles relative to 1 mole of the compound 3. In a situation in which the additive amount of the base is too small, reactivity may decrease. By contrast, in a situation in which the additive amount of the base is too large, reaction may be difficult to control.

Reaction R-3 may be carried out in a solvent. Examples of the solvent used in Reaction R-3 include the same as those listed as examples of the solvent used in Reaction R-2, for example. Reaction R-3 is preferably carried out at a reaction temperature of at least 0° C. and no greater than 50° C. and preferably has a reaction time of at least 2 hours and no greater than 24 hours.

(Reaction R-4)

In Reaction R-4, a compound 12 (1 chemical equivalent) is caused to react with triethyl phosphite (1 chemical equivalent) to yield a compound 13 (1 chemical equivalent).

In Reaction R-4, at least 1 mole and no greater than 2.5 moles of triethyl phosphite is preferably added relative to 1 mole of the compound 12. In a situation in which the number of moles of triethyl phosphite is too small relative to the number of moles of the compound 12, the percentage yield of the compound 13 may decrease. By contrast, in a situation in which the number of moles of triethyl phosphite is too large relative to the number of moles of the compound 12, unreacted triethyl phosphite may remain after reaction to make it difficult to purify the compound 13.

Reaction R-4 is preferably carried out at a reaction temperature of at least 160° C. and no greater than 200° C. and preferably has a reaction time of at least 2 hours and no greater than 10 hours.

(Reaction R-5)

In Reaction R-5, the compound 13 (1 chemical equivalent) is caused to react with the compound 7 (1 chemical equivalent) to yield the compound 8 (1 chemical equivalent). Reaction R-5 is a Wittig reaction.

In Reaction R-5, at least 1 mole and no greater than 2.5 moles of the compound 7 is preferably added relative to 1 mole of the compound 13. In a situation in which the number of moles of the compound 7 is too small relative to the number of moles of the compound 13, the percentage yield of the compound 8 may decrease. By contrast, in a situation in which the number of moles of the compound 7 is too large relative to the number of moles of the compound 13, unreacted compound 5 may remain after reaction to make it difficult to purify the compound 8.

Reaction R-5 may be carried out under the presence of a base. Examples of the base used in Reaction R-5 include the same bases as those listed as examples of the base used in Reaction R-2, for example. Any one of the above bases may be used or a combination of any two or more of the above base may be used. An additive amount of the base is preferably at least 1 mole and no greater than 2 moles relative to 1 mole of the compound 13. In a situation in which the additive amount of the base is too small, reactivity may decrease. By contrast, in a situation in which the additive amount of the base is too large, reaction may be difficult to control.

Reaction R-5 may be carried out in a solvent. Examples of the solvent used in Reaction R-5 include the same solvents as those listed as examples of the solvent used in Reaction R-2, for example. Reaction R-5 is preferably carried out at a reaction temperature of at least 0° C. and no greater than 50° C. and preferably has a reaction time of at least 2 hours and no greater than 24 hours.

(Synthesis of Triphenylamine Derivative 1-3)

The triphenylamine derivative 1-3 is synthesized according to Reaction R-6, for example.

In reaction formula (R-6), $R_1$, $R_2$, $R_3$, $R_4$, $R_5$, $R_{11}$, $R_{12}$, $R_{13}$, $R_{14}$, $R_{15}$, and n are equivalent to $R_1$, $R_2$, $R_3$, $R_4$, $R_5$, $R_{11}$, $R_{12}$, $R_{13}$, $R_{14}$, $R_{15}$, and n in general formula (1-1), respectively. Also, X represents a halogen atom.

In Reaction R-6, a compound 9 (1 chemical equivalent) is caused to react with the compound 8 (1 chemical equivalent) to produce the triphenylamine derivative 1-3 (1 chemical equivalent). Reaction R-6 is a coupling reaction.

In Reaction R-6, preferably, at least 1 mole and no greater than 5 moles of the compound 8 is added relative to 1 mole of the compound 9. In a situation in which the number of moles of compound 8 is too small relative to the number of moles of the compound 9, the percentage yield of the triphenylamine derivative 1-3 may decrease. By contrast, in a situation in which the number of moles of the compound 8 is too large relative to the number of moles of the compound 9, unreacted compound 8 may remain after reaction to make it difficult to purify the triphenylamine derivative 1-3.

Reaction R-6 is preferably carried out at a reaction temperature of at least 80° C. and no greater than 140° C. and preferably has a reaction time of at least 2 hours and no greater than 10 hours.

A palladium compound is preferably used as a catalyst in Reaction R-6. The use of the palladium compound tends to decrease activation energy in Reaction R-6. It is considered

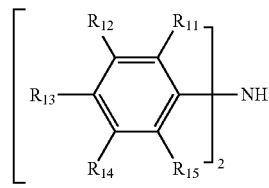

(9)

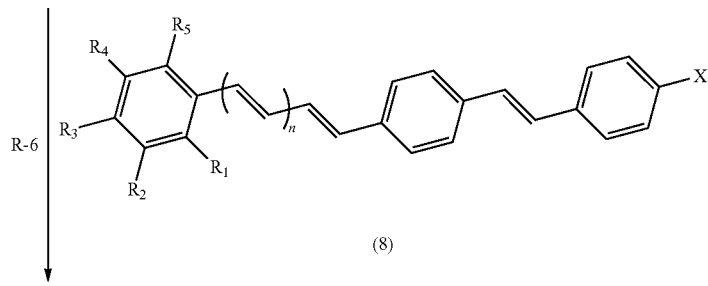

(8)

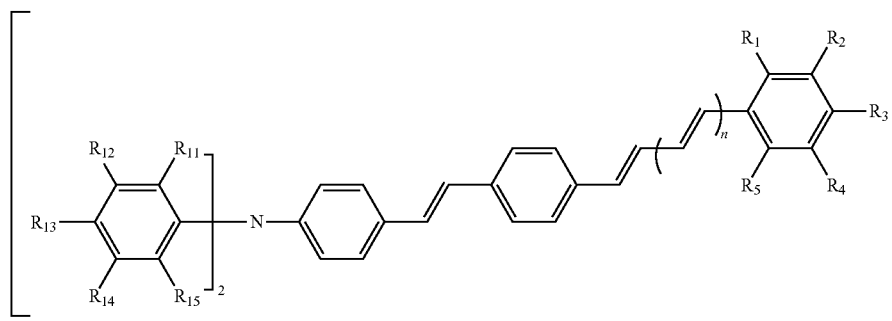

(1-3)

that the percentage yield of the triphenylamine derivative 1-3 can be increased as a result of the use of the palladium compound. Examples of palladium compounds that may be used include tetravalent palladium compounds, divalent palladium compounds, and other palladium compounds. Specific examples of tetravalent palladium compounds that can be used include hexachloro palladium (IV) sodium tetrahydrate and hexachloro palladium (IV) potassium tetrahydrate. Specific examples of divalent palladium compounds that can be used include palladium (II) chloride, palladium (II) bromide, palladium (II) acetate, palladium (II) acetylacetate, dichlorobis(benzonitrile)palladium(II), dichlorobis(triphenylphosphine)palladium(II), dichlorotetramine palladium(II), and dichloro(cycloocta-1,5-diene) palladium(II). Specific examples of the other palladium compounds that can be used include tris(dibenzylideneacetone)dipalladium(0), tris(dibenzylideneacetone)dipalladium(0) chloroform complex, and tetrakis(triphenylphosphine)palladium(0). Any one of the above palladium compounds may be used or a combination of any two or more of the above palladium compounds may be used. The additive amount of the palladium compound is preferably at least 0.0005 moles and no greater than 20 moles relative to 1 moles of the compound 9, and more preferably at least 0.001 moles and no greater than 1 mole.

A palladium compound such as described above may have a structure including a ligand. In the presence of a palladium compound having a structure including a ligand, reactivity of Reaction R-6 can be easily improved. Examples of ligands that may be used include tricyclohexylphosphine, triphenylphosphine, methyldiphenylphosphine, trifurylphosphine, tri(o-tolyl)phosphine, dicyclohexylphenylphosphine, tri(t-butyl)phosphine, 2,2'-bis(diphenylphosphino)-1, 1'-binaphthyl, and 2,2'-bis[(diphenylphosphino)diphenyl] ether. Any one of the above ligands may be used or a combination of any two or more of the above ligands may be used. The additive amount of the ligand is preferably at least 0.0005 moles and no greater than 20 moles relative to 1 mole of the compound 9, and more preferably at least 0.001 moles and no greater than 1 mole.

Reaction R-6 is preferably carried out under the presence of a base. Through a reaction under the presence of a base as above, halogenated hydrogen (for example, hydrogen chloride) that is generated during reaction can be rapidly neutralized to improve catalyst activity. It is considered that the percentage yield of the triphenylamine derivative 1-3 can be considered to be increased as a result. The base may be an inorganic base or an organic base. Examples of preferable organic bases that can be used include alkali metal alkoxides (specifically, sodium methoxide, sodium ethoxide, potassium methoxide, potassium ethoxide, lithium tert-butoxide, sodium tert-butoxide, or potassium tert-butoxide), with sodium tert-butoxide being particularly preferable. Examples of inorganic bases that can be used include tripotassium phosphate and caesium fluoride. In a situation in which at least 0.0005 moles and no greater than 20 moles of a palladium compound is added relative to 1 mole of the compound 9, the additive amount of the base is preferably at least 1 mole and no greater than 50 moles, and more preferably at least 1 mole and no greater than 30 moles.

Reaction R-6 may be carried out in a solvent. Examples of solvents that may be used include xylene (specifically, o-xylene), toluene, tetrahydrofuran, and dimethyl formamide.

(Synthesis of Triphenylamine Derivative 1-4)

The triphenylamine derivative 1-4 is synthesized according to Reaction R-7, for example.

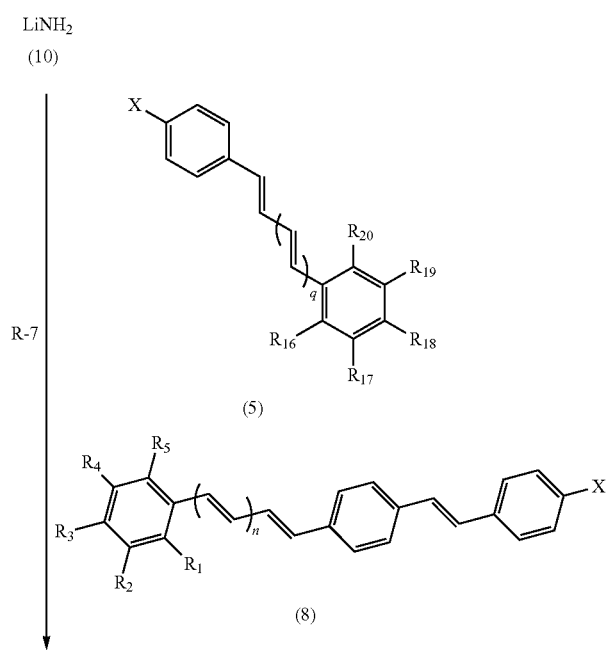

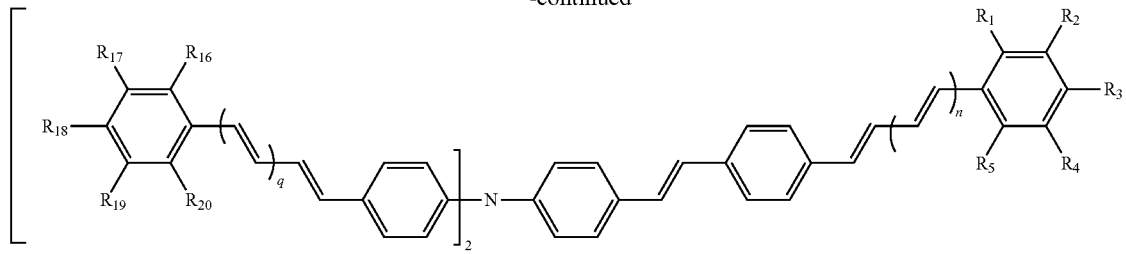

(1-4)

In reaction formula (R-7), $R_1$, $R_2$, $R_3$, $R_4$, $R_5$, $R_{16}$, $R_{17}$, $R_{18}$, $R_{19}$, $R_{20}$, n, and q are equivalent to $R_1$, $R_2$, $R_3$, $R_4$, $R_5$, $R_{16}$, $R_{17}$, $R_{18}$, $R_{19}$, $R_{20}$, n, and q in general formula (1-2), respectively. Also, X represents a halogen atom.

In Reaction R-7, a compound 10 (1 chemical equivalent) is caused to react with the compound 5 (2 chemical equivalents) and the compound 8 (1 chemical equivalent) to produce the triphenylamine derivative 1-3 (1 chemical equivalent). Reaction R-7 is a coupling reaction.

In Reaction R-7, at least 2 moles and no greater than 10 moles of the compound 5 and at least 1 mole and no greater than 5 moles of the compound 8 are preferably added relative to 1 mole of the compound 10. In a situation in which the respective numbers of moles of compounds 5 and 8 are too small relative to the number of moles of the compound 10, the percentage yield of the triphenylamine derivative 1-4 may decrease. By contrast, in a situation in which the respective numbers of moles of compounds 5 and 8 are too large relative to the number of moles of the compound 10, unreacted compounds 5 and 8 may remain after reaction to make it difficult to purify the triphenylamine derivative 1-4.

A preferable range of reaction temperature in Reaction R-7 is the same as that in Reaction R-6. A palladium compound is preferably used as a catalyst in Reaction R-7. Examples of the palladium compound used in Reaction R-7 include the same palladium compounds as those listed in examples of the compound used in Reaction R-6. A palladium compound such as described above may have a structure including a ligand. Examples of the ligand used in Reaction R-7 include the same ligands as those listed in examples of the ligand used in Reaction R-6. Reaction R-7 is preferably carried out under the presence of a base. Examples of the base used in Reaction R-7 includes the same as those listed as examples of the base used in Reaction R-6. Reaction R-7 may be carried out in a solvent. Examples of the solvent used in Reaction R-7 include the same solvents as those listed as examples of the solvent used in Reaction R-6.

The triphenylamine derivative 1-4 can be separated by refining a resultant reaction product of Reaction R-7. Purification is carried out according to silica gel chromatography, for example. A mixed solvent of chloroform and hexane (volume ratio 1:1) is used as a developing solvent, for example.

(Synthesis of Triphenylamine Derivative 1-5)

The triphenylamine derivative 1-5 is synthesized according to Reaction R-8, for example.

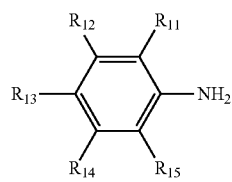

(11)

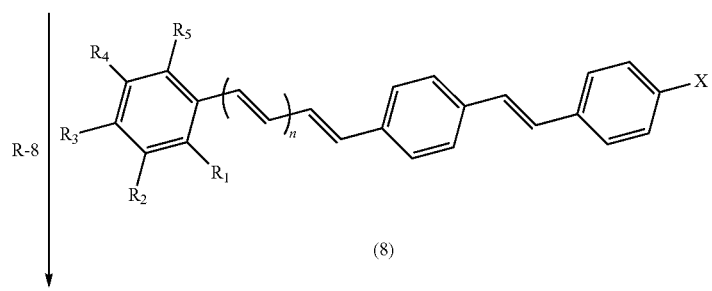

(8)

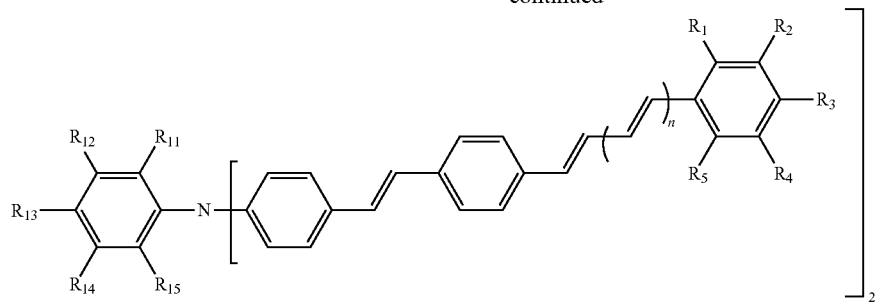

(1-5)

In reaction formula (R-8), $R_1$, $R_2$, $R_3$, $R_4$, $R_5$, $R_{11}$, $R_{12}$, $R_{13}$, $R_{14}$, $R_{15}$, and n are equivalent to $R_1$, $R_2$, $R_3$, $R_4$, $R_5$, $R_{11}$, $R_{12}$, $R_{13}$, $R_{14}$, $R_{15}$, and n in general formula (1-1), respectively. Also, X represents a halogen atom.

In Reaction R-8, a compound 11 (1 chemical equivalent) is caused to react with the compound 8 (2 chemical equivalents) to produce the triphenylamine derivative 1-5 (1 chemical equivalent). Reaction R-8 is a coupling reaction.

In Reaction R-8, at least 2 moles and no greater than 10 moles of the compound 8 is preferably added relative to 1 mole of the compound 11. In a situation in which the number of moles of the compounds 8 is too small relative to the number of moles of the compound 11, the percentage yield of the triphenylamine derivative 1-5 may decrease. By contrast, in a situation in which the number of moles of the compound 8 is too large relative to the number of moles of the compound 11, unreacted compound 8 may remain after reaction to make it difficult to purify the triphenylamine derivative 1-5.

A preferable range of reaction temperature in Reaction R-8 is the same as that in Reaction R-6. A palladium compound is preferably used as a catalyst in Reaction R-8. Examples of the palladium compound used in Reaction R-8 include the same palladium compounds as those listed as examples of the palladium compound used in Reaction R-6. A palladium compound such as described above may have a structure including a ligand. Examples of the ligand used in Reaction R-8 include the same ligands as those listed as examples of the ligand used in Reaction R-6. Reaction R-8 is preferably carried out under the presence of a base. Examples of the base used in Reaction R-8 include the same bases as those listed as examples of the base used in Reaction R-6. Reaction R-8 may be carried out in a solvent. Examples of the solvent used in Reaction R-8 includes the same as those listed as examples of the solvent used in Reaction R-6.

(Synthesis of Triphenylamine Derivative 1-6)

The triphenylamine derivative 1-6 is synthesized according to Reaction R-9, for example.

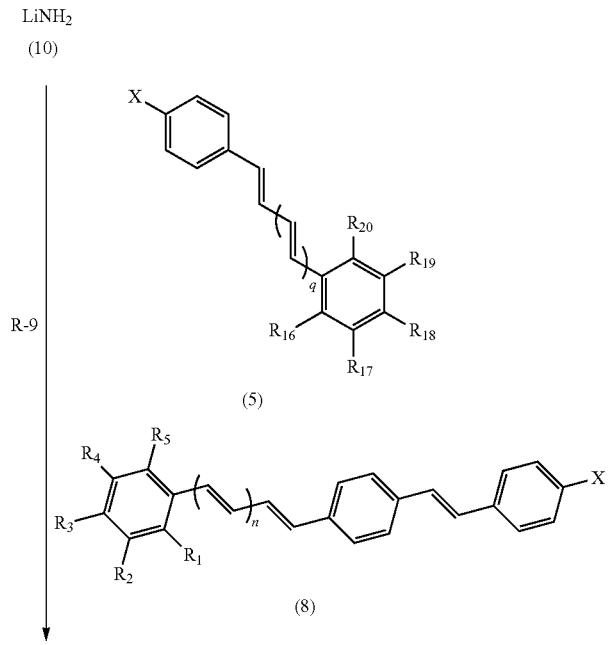

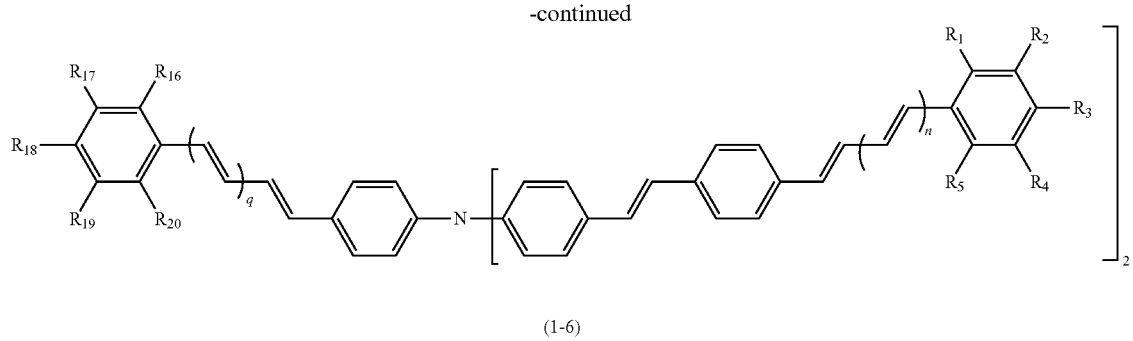

(1-6)

In reaction formula (R-9), $R_1$, $R_2$, $R_3$, $R_4$, $R_5$, $R_{16}$, $R_{17}$, $R_{18}$, $R_{19}$, $R_{20}$, n, and q are equivalent to $R_1$, $R_2$, $R_3$, $R_4$, $R_5$, $R_{16}$, $R_{17}$, $R_{18}$, $R_{19}$, $R_{20}$, n, and q in general formula (1-2), respectively. Also, X represents a halogen atom.

In Reaction R-9, the compound 10 (1 chemical equivalent) is caused to react with the compound 5 (1 chemical equivalent) and the compound 8 (2 chemical equivalents) to produce the triphenylamine derivative 1-6 (1 chemical equivalent). Reaction R-9 is a coupling reaction.

In Reaction R-9, at least 1 mole and no greater than 5 moles of the compound 5 and at least 2 moles and no greater than 10 moles of the compound 8 are preferably added relative to 1 mole of the compound 10. In a situation in which the respective numbers of moles of the compounds 5 and 8 are too small relative to the number of moles of the compound 10, the percentage yield of the triphenylamine derivative 1-6 may decrease. By contrast, in a situation in which the respective numbers of moles of the compounds 5 and 8 are too large relative to the number of moles of the compound 10, unreacted compounds 5 and 8 may remain after reaction to make it difficult to purify the triphenylamine derivative 1-6.

A preferable range of reaction temperature in Reaction R-9 is the same as that in Reaction R-6. A palladium compound is preferably used as a catalyst in Reaction R-9. Examples of the palladium compound used in Reaction R-9 include the same palladium compounds as those listed as examples of the palladium compound used in Reaction R-6. A palladium compound such as described above may have a structure including a ligand. Examples of the ligand used in Reaction R-9 include the same ligands as those listed as examples of the ligand used in Reaction R-6. Reaction R-9 is preferably carried out under the presence of a base. Examples of the base used in Reaction R-9 include the same bases as hose listed as examples of the base used in Reaction R-6. Reaction R-9 may be carried out in a solvent. Examples of the solvent used in Reaction R-9 include the same solvents as those listed as examples of the solvent used in Reaction R-6.

The triphenylamine derivative 1-6 can be separated by refining a resultant reaction product of Reaction R-9. Purification is carried out according to silica gel chromatography, for example. A mixed solvent of chloroform and hexane (volume ratio 1:1) is used as a developing solvent.

(Synthesis of Triphenylamine Derivative 1-7)

The triphenylamine derivative 1-7 is synthesized according to Reaction R-10, for example.

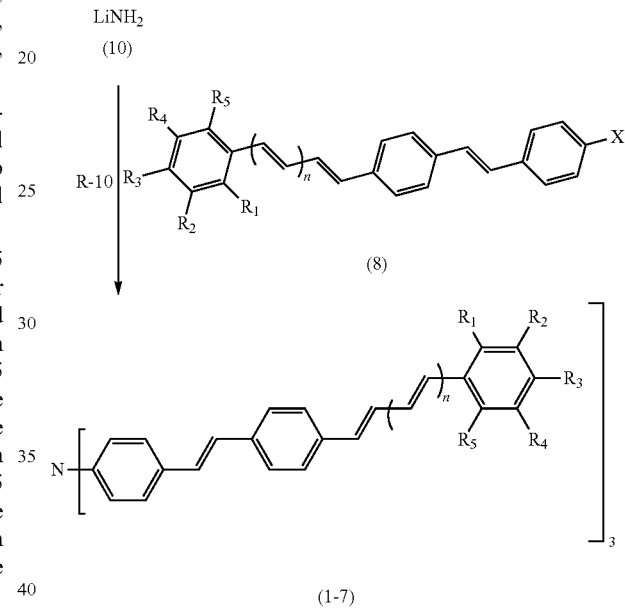

(1-7)

In reaction formula (R-10), $R_1$, $R_2$, $R_3$, $R_4$, $R_5$, and n are equivalent to $R_1$, $R_2$, $R_3$, $R_4$, $R_5$, and n in general formulas (1-1) and (1-2), respectively. Also, X represents a halogen atom.

In Reaction R-10, the compound 10 (1 chemical equivalent) is caused to react with the compound 8 (3 chemical equivalents) to produce the triphenylamine derivative 1-7 (1 chemical equivalent). The Reaction R-10 is a coupling reaction.

In Reaction R-10, at least 3 moles and no greater than 15 moles of the compound 8 is preferably added relative to 1 mole of the compound 10. In a situation in which the number of moles of the compounds 8 is too small relative to the number of moles of the compound 10, the percentage yield of the triphenylamine derivative 1-7 may decrease. By contrast, in a situation in which the number of moles of the compound 8 is too large relative to the number of moles of the compound 10, unreacted compound 8 may remain after reaction to make it difficult to purify the triphenylamine derivative 1-7.

A preferable range of reaction temperature in Reaction R-10 is the same as that n Reaction R-6. A palladium compound is preferably used as a catalyst in Reaction R-10. Examples of the palladium compound used in Reaction R-10 include the same palladium compounds as those listed as examples of the palladium compound used in Reaction R-6. A palladium compound such as described above may have a structure including a ligand. Examples of the ligand used in Reaction R-10 include the same ligands as those listed as examples of the ligand used in Reaction R-6. Reaction R-10 is preferably carried out under the presence of a base. Examples of the base used in Reaction R-10 include the same bases as those listed as examples of the base used in Reaction R-6. Reaction R-10 may be carried out in a solvent. Examples of the solvent used in Reaction R-10 include the same solvents as those listed as examples of the solvent used in Reaction R-6.

Through the above, a description of the triphenylamine derivative according to the present embodiment has been provided. The triphenylamine derivative according to the present embodiment, when contained in the photosensitive layer of the electrophotographic photosensitive member, can improve electric properties of the electrophotographic photosensitive member.

Second Embodiment: Electrophotographic Photosensitive Member

A second embodiment is directed to an electrophotographic photosensitive member (also referred to below as a photosensitive member). The photosensitive member may be a single-layer photosensitive member or a multi-layer photosensitive member. The photosensitive member includes a photosensitive layer. The photosensitive layer contains at least a charge generating material and a triphenylamine derivative 1 according to the first embodiment as a hole transport material.

<1. Multi-Layer Photosensitive Member>

Figure 4A:
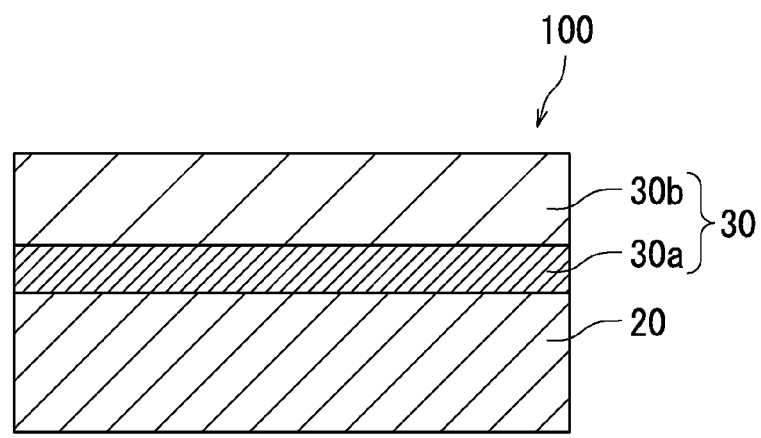
FIGS. 4A, 4B, and 4C each are a schematic cross sectional view illustrating an example of an electrophotographic photosensitive member according to a second embodiment of the present disclosure.
Figure 4B:
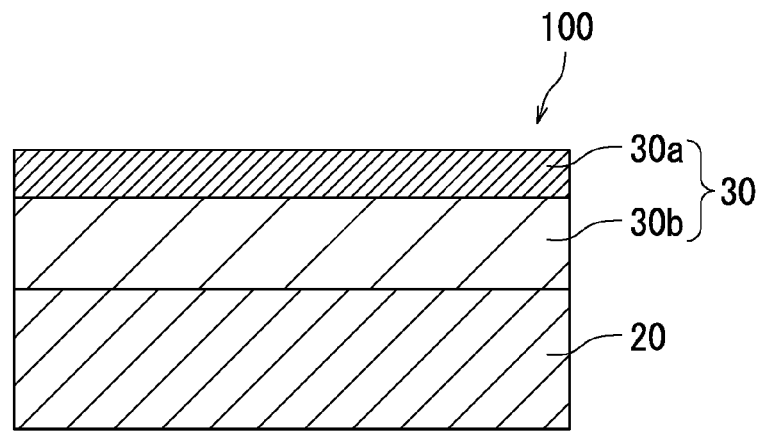
Figure 4C:
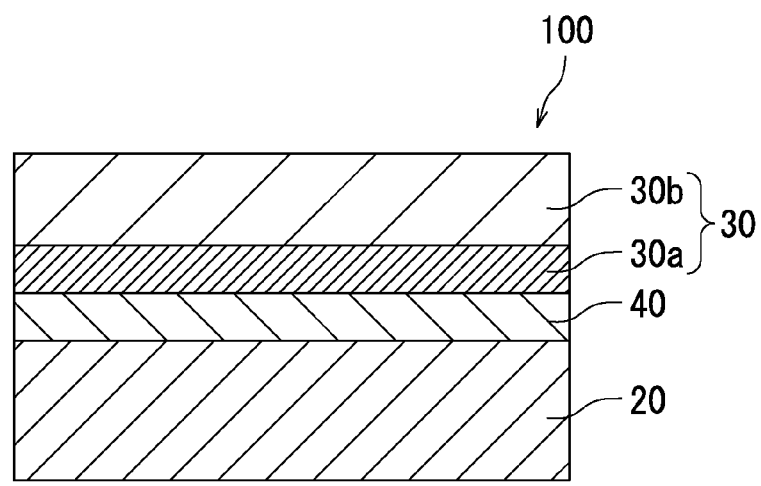

Following describes a configuration in which a photosensitive member 100 is a multi-layer photosensitive member with reference to FIGS. 4A-4C. FIGS. 4A-4C each are a schematic cross sectional view illustrating a multi-layer photosensitive member that is an example of the photosensitive member 100 according to the present embodiment.

As illustrated in FIG. 4A, the multi-layer photosensitive member that is the photosensitive member 100 includes a conductive substrate 20 and a photosensitive layer 30. The multi-layer photosensitive member includes as the photosensitive layer 30, a charge generating layer 30a and a charge transport layer 30b. Note that the conductive substrate 20 will be described later.

As illustrated in FIG. 4B, the charge transport layer 30b may be disposed on the conductive substrate 20 and the charge generating layer 30a may be disposed on the charge transport layer 30b in the multi-layer photosensitive member that is the photosensitive member 100. Typically, the charge transport layer 30b has a film thickness thicker than the charge generating layer 30a and therefore is hardly broken when compared with the charge generating layer 30a. For this reason, it is preferable as illustrated in FIG. 4A to dispose the charge transport layer 30b on the charge generating layer 30a in order to improve abrasion resistance of the multi-layer photosensitive member.

As illustrated in FIG. 4C, the multi-layer photosensitive member that is the photosensitive member 100 may include an intermediate layer (undercoat layer) 40 in addition to the conductive substrate 20 and the photosensitive layer 30. The intermediate layer 40 is disposed between the conductive substrate 20 and the photosensitive layer 30. In addition, a protective layer (not illustrated) may be disposed on the photosensitive layer 30.

No particular limitations are placed on thicknesses of the charge generating layer 30a and the charge transport layer 30b so long as the thicknesses thereof are sufficient to enable the charge generating layer 30a and the charge transport layer 30b to implement their respective functions. The charge generating layer 30a preferably has a thickness of at least 0.01 µm and no greater than 5 µm, and more preferably at least 0.1 µm and no greater than 3 µm. The charge transport layer 30b preferably has a thickness of at least 2 µm and no greater than 100 µm, and more preferably at least 5 µm and no greater than 50 µm.

The charge generating layer 30a of the photosensitive layer 30 contains a charge generating material. The charge generating layer 30a may optionally contain a binder resin for charge generating layer formation (also referred to below as a base resin) and various additives depending on necessity thereof. The charge generating material, the base resin, and the additives will be described later.

The charge transport layer 30b of the photosensitive layer 30 contains a hole transport material. The charge transport layer 30b may optionally contain a binder resin, an electron acceptor compound, and various additives depending on necessity thereof. The hole transport material, the binder resin, the electron acceptor compound, and the additives will be described later. The configuration in which the photosensitive member 100 is a multi-layer photosensitive member has been described so far with reference to FIGS. 4A-4C.

<2. Single-Layer Photosensitive Member>

Figure 5A:
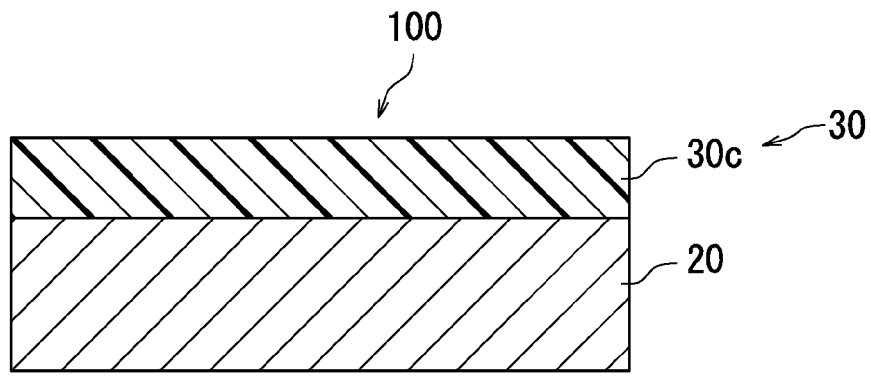
FIGS. 5A, 5B, and 5C each are a schematic cross sectional view illustrating another example of the electrophotographic photosensitive member according to the second embodiment of the present disclosure.
Figure 5B:
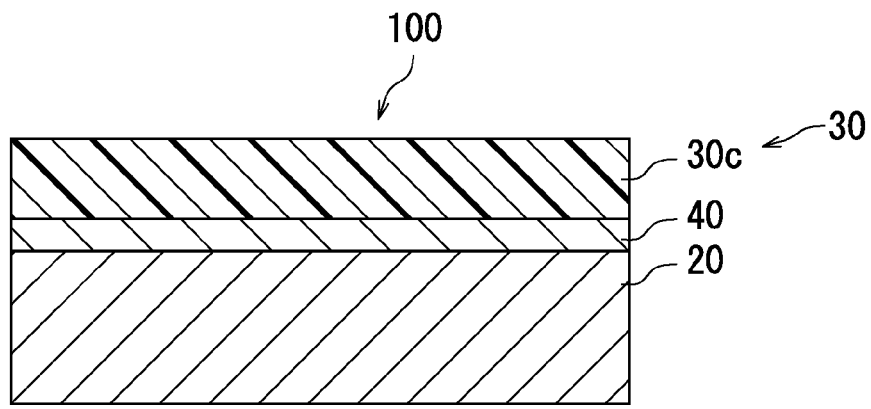
Figure 5C:
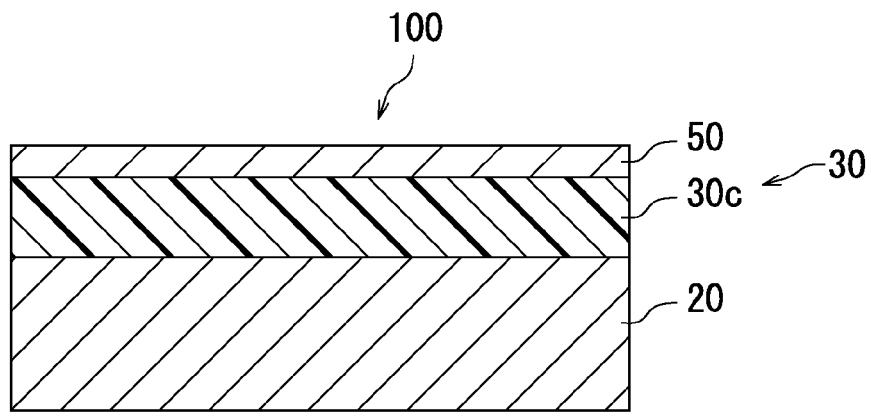

Following describes a configuration in which the photosensitive member 100 is a single-layer photosensitive member with reference to FIGS. 5A-5C. FIGS. 5A-5C each are a schematic cross sectional view illustrating a single-layer photosensitive member as another example of the photosensitive member 100 according to the present embodiment.

As illustrated in FIG. 5A, the single-layer photosensitive member that is the photosensitive member 100 includes a conductive substrate 20 and a photosensitive layer 30. The single-layer photosensitive member as the photosensitive member 100 includes a single-layer type photosensitive layer 30c that is the photosensitive layer 30. Note that the conductive substrate 20 will be described later.

As illustrated in FIG. 5B, the single-layer photosensitive member that is the photosensitive member 100 may include an intermediate layer (undercoat layer) 40 in addition to the single-layer type photosensitive layer 30c and the conductive substrate 20. The intermediate layer 40 is disposed between the conductive substrate 20 and the single-layer type photosensitive layer 30c. Furthermore, as illustrated in FIG. 5C, a protective layer 50 may be disposed on the single-layer type photosensitive layer 30c.

No particular limitations are placed on thickness of the single-layer type photosensitive layer 30c, so long as the thickness thereof is sufficient to enable the single-layer type photosensitive layer to function as a single-layer type photosensitive layer. The single-layer type photosensitive layer 30c preferably has a thickness of at least 5 µm and no greater than 100 µm, and more preferably at least 10 µm and no greater than 50 µm.

The single-layer type photosensitive layer 30c that is the photosensitive layer 30 contains a charge generating material and a hole transport material. The single-layer type photosensitive layer 30c may optionally contain an electron transport material, a binder resin, and various additives depending on necessity thereof. The hole transport material, the charge generating material, the electron transport material, the binder resin, and the additives will be described later. A configuration in which the photosensitive member 100 is a single-layer photosensitive member has been described so far with reference to FIGS. 5A-5C.

The following describes elements common among the multi-layer photosensitive member and the single-layer photosensitive member that each are the photosensitive member.

<3. Conductive Substrate>

No particular limitations are places on the conductive substrate other than being a conductive substrate that can be used in a photosensitive member. It is only required that at least a surface portion of the conductive substrate is made from a conductive material. An example of the conductive substrate is a conductive substrate made from a conductive material. Another example of the conductive substrate is a conductive substrate covered with a conductive material. Examples of conductive materials that can be used include aluminum, iron, copper, tin, platinum, silver, vanadium, molybdenum, chromium, cadmium, titanium, nickel, palladium, indium, stainless steel, and brass. Any one of the conductive materials listed above may be used or a combination of any two or more of the conductive materials listed above may be used (for example, as an alloy). Among the conductive materials listed above, aluminum or an aluminum alloy is preferable in terms of excellent charge mobility from the photosensitive layer to the conductive substrate.

The conductive substrate is not limited to being any particular shape and the shape thereof can be selected appropriately in accordance with the structure of an image forming apparatus in which the conductive substrate is to be used. The conductive substrate is for example a sheet or drum. In addition, the conductive substrate is not limited to having any particular thickness and the thickness thereof can be selected appropriately in accordance with the shape of the conductive substrate.

<4. Hole Transport Material>

The photosensitive layer contains a triphenylamine derivative 1 according to the first embodiment as a hole transport material. In a configuration in which the photosensitive member is a multi-layer photosensitive member, the charge transport layer contains the triphenylamine derivative 1 as a hole transport material. In a configuration in which the photosensitive member is a single-layer photosensitive member, the single-layer type photosensitive layer contains the triphenylamine derivative 1 as a hole transport material. In a configuration in which the photosensitive layer contains the triphenylamine derivative 1, electric properties of the photosensitive member can be improved as described in the first embodiment.

<5. Charge Generating Material>

In a configuration in which the photosensitive member is a multi-layer photosensitive member, the charge generating layer contains a charge generating material. In a configuration in which the photosensitive member is a single-layer photosensitive member, the single-layer type photosensitive layer contains the charge generating material.

No particular limitations are placed on the charge generating material other than being a charge generating material that can be used in photosensitive members. Examples of charge generating materials that may be used include phthalocyanine-based pigments, perylene-based pigments, bisazo pigments, tris-azo pigments, dithioketopyrrolopyrrole pigments, metal-free naphthalocyanine pigments, metal naphthalocyanine pigments, squaraine pigments, indigo pigments, azulenium pigments, cyanine pigments, powders of inorganic photoconductive materials (for example, selenium, selenium-tellurium, selenium-arsenic, cadmium sulfide, or amorphous silicon), pyrylium pigments, anthanthrone-based pigments, triphenylmethane-based pigments, threne-based pigments, toluidine-based pigments, pyrazoline-based pigments, and quinacridone-based pigments.

Examples of phthalocyanine-based pigments include a metal-free phthalocyanine represented by chemical formula (CG-1) and metal phthalocyanines. Examples of metal phthalocyanines include titanyl phthalocyanine represented by chemical formula (CG-2), hydroxygallium phthalocyanine, and chlorogallium phthalocyanine. A phthalocyanine-based pigment that is used may be crystalline or non-crystalline. The phthalocyanine-based pigmen that is used is not limited to having any particular crystal structure (for example, an α-form crystal structure, a β-form crystal structure, a Y-form crystal structure, a V-form crystal structure, or a II-form crystal structure), and a phthalocyanine-based pigment having any crystal structure may be used.

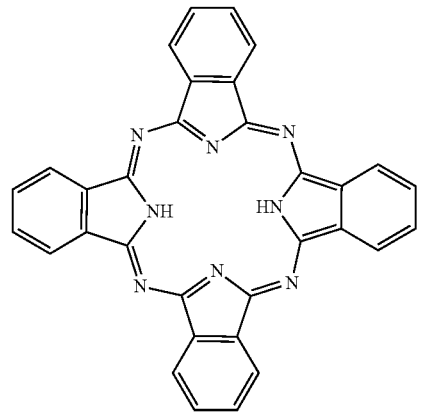

(CG-1)

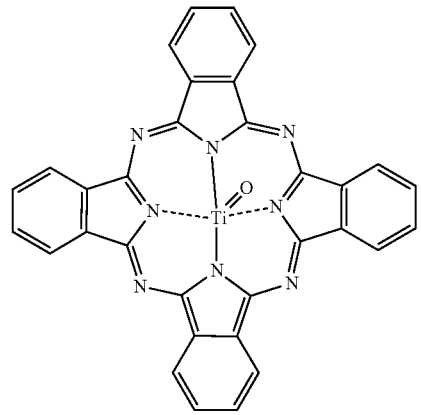

(CG-2)

Examples of crystals that a metal-free phthalocyanine may have include an X-form crystal structure for metal-free phthalocyanine. The metal free phthalocyanine having an X-form crystal structure may also be referred to below as an X-form metal-free phthalocyanine. Examples of crystal structures that a titanyl phthalocyanine may have include α-form, β-form, and Y-form crystal structures for titanyl phthalocyanine. The titanyl phthalocyanines having α-form, β-form, and Y-form crystal structures may also be referred to below as α-form, β-form, and Y-form titanyl phthalocyanines, respectively. Examples of crystal structures that a hydroxygallium phthalocyanine may have include a V-form crystal structure for hydroxygallium phthalocyanine. Examples of crystal structures that a chlorogallium phthalocyanine may have include a II-form crystal structure for chlorogallium phthalocyanine. In terms of high quantum yield in a wavelength range of at least 700 nm, an X-form metal-free phthalocyanine or a Y-form titanyl phthalocyanine is preferable. In order to particularly improve electric properties in a configuration in which the photosensitive layer contains the triphenylamine derivative 1 as a hole transport material, a Y-form titanyl phthalocyanine is further preferable.

In a CuKα characteristic X-ray diffraction spectrum, a Y-form titanyl phthalocyanine has for example a main peak at a Bragg angle (2θ±0.2°) of 27.2°. The term main peak refers to a most intense or second most intense peak within a range of Bragg angles (2θ±0.2°) from 3° to 40° in a CuKα characteristic X-ray diffraction spectrum.

(Method for Measuring CuKα Characteristic X-ray Diffraction Spectrum)

An example of a method for measuring a CuKα characteristic X-ray diffraction spectrum will be described below. A sample (titanyl phthalocyanine) is loaded into a sample holder of an X-ray diffraction spectrometer (for example, a RINT (registered Japanese trademark) 1100 produced by Rigaku Corporation), and an X-ray diffraction spectrum is measured using a Cu X-ray tube, a tube voltage of 40 kV, a tube current of 30 mA, and X-rays characteristic of CuKα having a wavelength of 1.542 Å. The measurement range (2θ) is for example from at least 3° and no greater than 40° (start angle 3°, stop angle 40°), and the scanning speed is for example 10°/minute.

A single charge generating material having an absorption wavelength in a desired region may be used, or a combination of two or more of such charge generating materials may be used. For example, in a digital optical image forming apparatus (for example, a laser beam printer or facsimile machine that uses a light source such as a semiconductor laser), a photosensitive member that is sensitive to a region of wavelengths of at least 700 nm is preferably used. In order to use such a photosensitive member, a phthalocyanine-based pigment is preferably used, for example. A metal-free phthalocyanine or a titanyl phthalocyanine is more preferable, and an X-form metal-free phthalocyanine or a Y-form titanyl phthalocyanine is particularly preferable. Any one type of charge generating material may be used or a combination of any two or more types of charge generating materials may be used.

A photosensitive member included in an image forming apparatus that uses a short-wavelength laser light source (for example, a laser light source having an approximate wavelength of at least 350 nm and no greater than 550 nm) preferably contains an anthanthrone-based pigment as a charge generating material.

In a configuration in which the photosensitive member is a multi-layer photosensitive member, the amount of the charge generating material contained in the charge generating layer is preferably at least 5 parts by mass and no greater than 1,000 parts by mass relative to 100 parts by mass of a base resin contained in the charge generating layer, and more preferably at least 30 parts by mass and no greater than 500 parts by mass.

In a configuration in which the photosensitive member is a single-layer type photosensitive layer, the amount of the charge generating material contained in the single-layer photosensitive member is preferably at least 0.1 parts by mass and no greater than 50 parts by mass relative to 100 parts by mass of a binder resin contained in the single-layer type photosensitive layer, and more preferably at least 0.5 parts by mass and no greater than 30 parts by mass.

<6. Electron Transport Material and Electron Acceptor Compound>

In a configuration in which the photosensitive member is a multi-layer photosensitive member, the charge transport layer may contain an electron acceptor compound depending on necessity thereof. Inclusion of the electron acceptor compound tends to improve hole transport by the hole transport material. By contrast, in a configuration in which the photosensitive member is a single-layer photosensitive member, the single-layer type photosensitive layer may contain an electron transport material depending on necessity thereof. Through inclusion of the electron transport material, the single-layer type photosensitive layer can transport electrons and the single-layer type photosensitive layer can be easily provided with bipolar properties.

Examples of electron transport materials or electron acceptor compounds include quinone-based compounds, diimide-based compounds, hydrazone-based compounds, malononitrile-based compounds, thiopyran-based compounds, trinitrothioxanthone-based compounds, 3,4,5,7-tetranitro-9-fluorenone-based compounds, dinitroanthracene-based compounds, dinitroacridine-based compounds, tetracyanoethylene, 2,4,8-trinitrothioxanthone, dinitrobenzene, dinitroacridine, succinic anhydride, maleic anhydride, and dibromomaleic anhydride. Examples of quinone-based compounds include diphenoquinone-based compounds, azoquinone-based compounds, anthraquinone-based compounds, naphthoquinone-based compounds, nitoroanthraquinone-based compounds, and dinitroanthraquinone-based compounds. Any one of the electron transport materials listed above may be used or a combination of any two or more of the electron transport materials listed above may be used. Any one of the electron acceptor compounds listed above may be used or a combination of any two or more of the electron acceptor compounds listed above may be used.

Examples of electron transport materials or electron acceptor compounds include compounds represented by general formulas (14)-(16).

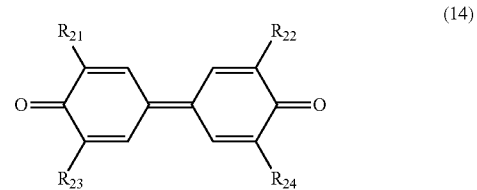

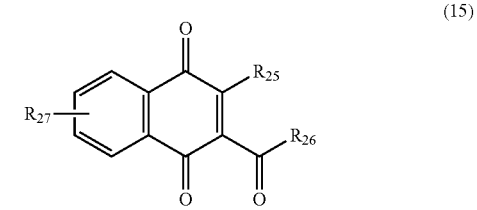

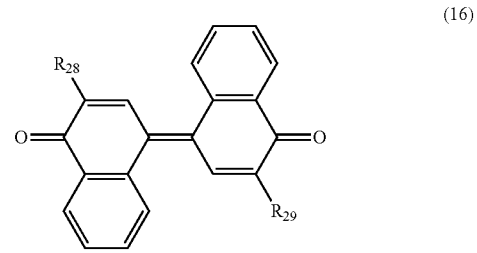

In general formulas (14)-(16), $R_{21}$-$R_{29}$ each represent, independently of one another, a hydrogen atom, a cyano group, an optionally substituted alkyl group, an optionally substituted alkenyl group, an optionally substituted alkoxy group, an optionally substituted alkoxycarbonyl group, an optionally substituted aryl group, or an optionally substituted heterocyclic group.

The alkyl group that can be represented by $R_{21}$-$R_{29}$ in general formulas (14)-(16) is for example an alkyl group having a carbon number of at least 1 and no greater than 6. The alkyl group having a carbon number of at least 1 and no greater than 6 is preferably an alkyl group having a carbon number of at least 1 and no greater than 5, and more preferably a methyl group, a 1,1-dimethylpropyl group, or a tert-butyl group. The alkyl group may be optionally substituted. Examples of possible substituents include a halogen atom, a hydroxyl group, alkoxy groups having a carbon number of at least 1 and no greater than 6, optionally substituted aryl groups having a carbon number of at least 6 and no greater than 14, and a cyano group. Although no particular limitations are placed on the number of substituents of the alkyl group, the alkyl group preferably has no greater than three substituents. Examples of possible substituents of the aryl group having a carbon number of at least 6 and no greater than 14 include a halogen atom, a hydroxyl group, alkyl groups having a carbon number of at least 1 and no greater than 6, alkoxy groups having a carbon number of at least 1 and no greater than 6, a nitro group, a cyano group, alkanoyl groups having a carbon number of at least 2 and no greater than 7 (carbonyl groups to which an alkyl group having a carbon number of at least 1 and no greater than 6 is bonded), a benzoyl group, a phenoxy group, alkoxycarbonyl groups having a carbon number of at least 2 and no greater than 7 (carbonyl groups to which an alkoxy group having a carbon number of at least 1 and no greater than 6 is bonded), and a phenoxycarbonyl group.

The alkenyl group that can be represented by $R_{21}$-$R_{29}$ in general formulas (14)-(16) is for example an alkenyl group having a carbon number of at least 2 and no greater than 6. The alkenyl group may be optionally substituted. Examples of possible substituents include a halogen atom, a hydroxyl group, alkoxy groups having a carbon number of at least 1 and no greater than 6, aryl groups having a carbon number of at least 6 and no greater than 14, and a cyano group. Although no particular limitations are placed on the number of substituents of the alkenyl group, the alkenyl group preferably has no greater than three substituents.

The alkoxy group that can be represented by $R_{21}$-$R_{29}$ in general formulas (14)-(16) is for example an alkoxy group having a carbon number of at least 1 and no greater than 6. The alkoxy group having a carbon number of at least 1 and no greater than 6 is preferably an alkoxy group having a carbon number of at least 1 and no greater than 3, and more preferably a methoxy group. The alkoxy group may be optionally substituted. Examples of possible substituents include a halogen atom, a hydroxyl group, alkoxy groups having a carbon number of at least 1 and no greater than 6, aryl groups having a carbon number of at least 6 and no greater than 14, and a cyano group. A preferable substituent of the alkoxy group is a phenyl group. Although no particular limitations are placed on the number of substituents of the alkoxy group, the alkoxy group preferably has no greater than three substituents, and more preferably one substituent.

The alkoxycarbonyl group that can be represented by $R_{21}$-$R_{29}$ in general formulas (14)-(16) is for example an alkoxycarbonyl group having a carbon number of at least 2 and no greater than 7. The alkoxycarbonyl group having a carbon number of at least 2 and no greater than 7 is a carbonyl group to which a straight- or branched-chain unsubstituted alkoxy group having a carbon number of at least 1 and no greater than 6 is bonded. The alkoxycarbonyl group may be optionally substituted. Examples of possible substituents include a halogen atom, a hydroxyl group, alkoxy groups having a carbon number of at least 1 and no greater than 6, aryl groups having a carbon number of at least 6 and no greater than 14, and a cyano group. Although no particular limitations are placed on the number of substituents of the alkoxycarbonyl group, the alkoxycarbonyl group preferably has no greater than three substituents.

The aryl group that can be represented by $R_{21}$-$R_{29}$ in general formulas (14)-(16) is for example an aryl group having a carbon number of at least 6 and no greater than 14. A preferable aryl group having a carbon number of at least 6 and no greater than 14 is a phenyl group. The aryl group may be optionally substituted. Examples of possible substituents include a halogen atom, a hydroxyl group, alkyl groups having a carbon number of at least 1 and no greater than 6, alkoxy group having a carbon number of at least 1 and no greater than 6, a nitro group, a cyano group, alkanoyl groups having a carbon number of at least 2 and no greater than 7 (carbonyl groups to which an alkyl group having a carbon number of at least 1 and no greater than 6 is bonded), a benzoyl group, a phenoxy group, alkoxycarbonyl groups having a carbon number of at least 2 and no greater than 7 (carbonyl groups to which an alkoxy group having a carbon number of at least 1 and no greater than 6 is bonded), a phenoxycarbonyl group, aryl groups having a carbon number of at least 6 and no greater than 14, and a biphenyl group. Although no particular limitations are placed on the number of substituents of the aryl group, the aryl group preferably has no greater than three substituents.

Examples of the heterocyclic group that can be represented by $R_{21}$-$R_{29}$ in general formulas (14)-(16) include: a heterocyclic group that is a 5- or 6-membered monocyclic ring containing 1 or more heteroatoms selected from the group consisting of N, S, and O; heterocyclic groups resulting from condensation of a plurality of such monocyclic rings; and heterocyclic groups resulting from condensation of such a monocylic ring with a five or six member hydrocarbon ring. In a configuration in which the heterocyclic group has a condensed ring structure, the condensed ring structure preferably includes no greater than three rings. Examples of possible substituents of the heterocyclic group include a halogen atom, a hydroxyl group, alkyl groups having a carbon number of at least 1 and no greater than 6, alkoxy groups having a carbon number of at least 1 and no greater than 6, a nitro group, a cyano group, alkanoyl group having a carbon number of at least 2 and no greater than 7 (carbonyl groups to which an alkyl group having a carbon number of at least 1 and no greater than 6 is bonded), a benzoyl group, a phenoxy group, alkoxycarbonyl groups having a carbon number of at least 2 and no greater than 7 (carbonyl groups to which an alkoxy group having a carbon number of at least 1 and no greater than 6 is bonded), and a phenoxycarbonyl group. Although no particular limitations are placed on the number of substituents of the heterocycli group, the heterocycligroup preferably has no greater than three substituents.

In a configuration in which the photosensitive layer is a single-layer type photosensitive layer containing a triphenylamine derivative 1 as a hole transport material, the single-layer type photosensitive layer preferably contains a compound represented by general formula (16) as an electron transport material in order to improve electric properties of the photosensitive member.

Specific examples of the compounds represented by general formulas (14)-(16) include compounds represented by chemical formulas (ET-1) and (ET-4). Hereinafter, the compounds represented by chemical formulas (ET-1) and (ET-4) may be referred to as compounds ET-1 and ET-4, respectively.

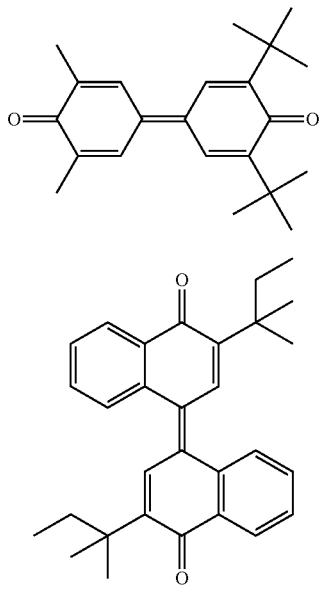

(ET-1)

(ET-4)

In a configuration in which the photosensitive member is a multi-layer photosensitive member, the amount of the electron acceptor compound contained in the charge transport layer is preferably at least 0.1 parts by mass and no greater than 20 parts by mass relative to 100 parts by mass of a binder resin contained in the charge transport layer, and more preferably at least 0.5 parts by mass and no greater than 10 parts by mass.

In a configuration in which the photosensitive member is a single-layer type photosensitive layer, the amount of the electron transport material contained in the single-layer photosensitive member is preferably at least 5 parts by mass and no greater than 100 parts by mass relative to 100 parts by mass of a binder resin contained in the single-layer type photosensitive layer, and more preferably at least 10 parts by mass and no greater than 80 parts by mass.

<7. Binder Resin>

In a configuration in the photosensitive member is a multi-layer photosensitive member, the charge transport layer contains a binder resin. In a configuration in which the photosensitive member is a single-layer photosensitive member, the single-layer type photosensitive layer contains a binder resin.

Examples of binder resins that can be used include thermoplastic resins, thermosetting resins, and photocurable resins. Examples of thermoplastic resins that can be used include polycarbonate resins, polyarylate resins, styrene-butadiene copolymers, styrene-acrylonitrile copolymers, styrene-maleic acid copolymers, acrylic acid polymers, styrene-acrylic acid copolymers, polyethylene resins, ethylene-vinyl acetate copolymers, chlorinated polyethylene resins, polyvinyl chloride resins, polypropylene resins, ionomer resins, vinyl chloride-vinyl acetate copolymers, alkyd resins, polyamide resins, urethane resins, polysulfone resins, diallyl phthalate resins, ketone resins, polyvinyl butyral resins, polyester resins, and polyether resins. Examples of thermosetting resins that can be used include silicone resins, epoxy resins, phenolic resins, urea resins, and melamine resins. Examples of photocurable resins that can be used include epoxy acrylates (acrylic acid adducts of epoxy compounds) and urethane acrylates (acrylic acid adducts of urethane compounds). Any one of the binder resins listed above may be used or a combination of any two or more of the binder resins listed above may be used.

Among the binder resins listed above, polycarbonate resins are preferable in order to obtain a single-layer type photosensitive layer and a charge transport layer having excellent balance in terms of processability, mechanical properties, optical properties, and abrasion resistance. Examples of polycarbonate resins that can be used include a bisphenol Z polycarbonate resin, a bisphenol ZC polycarbonate resin, a bisphenol C polycarbonate resin, and a bisphenol A polycarbonate resin.

The binder resin preferably has a viscosity average molecular weight of at least 40,000, and more preferably at least 40,000 and no greater than 52,500. In a configuration in which the binder resin has a viscosity average molecular weight of at least 40,000, abrasion resistance of the photosensitive member can be easily improved. In a configuration in which the binder resin has a viscosity average molecular weight of no greater than 52,500, the binder resin can readily dissolve in a solvent in formation of the photosensitive layer and an application liquid for charge transport layer formation or single-layer type photosensitive layer formation can be prevented from excessively increasing in viscosity. As a result, the charge transport layer or the single-layer type photosensitive layer can be easily formed.

<8. Base Resin>

In a configuration in which the photosensitive member is a multi-layer photosensitive member, the charge generating layer contains a base resin. No particular limitations are placed on the base resin other than being a base resin that can be used in a photosensitive member. Examples of base resins that can be used include thermoplastic resins, thermosetting resins, and photocurable resins. Examples of thermoplastic resins that can be used include styrene-butadiene copolymers, styrene-acrylonitrile copolymers, styrene-maleic acid copolymers, styrene-acrylic acid copolymers, acrylic acid polymers, polyethylene resins, ethylene-vinyl acetate copolymers, chlorinated polyethylene resins, polyvinyl chloride resins, polypropylene resins, ionomers, vinyl chloride-vinyl acetate copolymers, alkyd resins, polyamide resins, urethane resins, polycarbonate resins, polyarylate resins, polysulfone resins, diallyl phthalate resins, ketone resins, polyvinyl butyral resins, polyether resins, and polyester resins. Examples of thermosetting resins that can be used include silicone resins, epoxy resins, phenolic resins, urea resins, melamine resins, and other crosslinkable thermosetting resins. Examples of photocurable resins that can be used include epoxy acrylates (acrylic acid adducts of epoxy compounds) and urethane acrylates (acrylic acid adduct of urethane compounds). Any one of the base resins listed above may be used or a combination of any two or more of the base resins listed above may be used.

The base resin contained in the charge generating layer is preferably different from the base resin contained in the charge transport layer. In production of a multi-layer photosensitive member, a charge generating layer is formed on a conductive substrate and a charge transport layer is formed on the charge generating layer, for example. In the above production, an application liquid for charge transport layer formation is applied onto the charge generating layer. As a consequence, the charge generating layer is required to be insoluble in a solvent of the application liquid for charge transport layer formation.

<9. Additives>

The photosensitive layer (charge generating layer, charge transport layer, or single-layer type photosensitive layer) of the photosensitive member may contain various additives depending on necessity thereof. Examples of additives that may be used include antidegradants (for example, an antioxidant, a radical scavenger, a singlet quencher, or a ultraviolet absorbing agent), softeners, surface modifiers, bulking agents, thickeners, dispersion stabilizers, waxes, acceptors, donors, surfactants, plasticizers, sensitizers, and leveling agents. Specific examples of antioxidants include hindered phenols (for example, di(tert-butyl)p-cresol), hindered amine, paraphenylenediamine, arylalkane, hydroquinone, spirochromane, spiroindanone, derivatives of any of the above compounds, an organosulfur compound, or an organophosphorus compound.

<10. Intermediate Layer>

The intermediate layer (undercoat layer) contains for example inorganic particles and a resin for intermediate layer use (intermediate layer resin). It is thought that the presence of the intermediate layer can maintain an insulating state to an extent that leakage can be satisfactorily prevented from occurring and an electric current generated in exposure of the photosensitive member can be allowed to smoothly flow, thereby suppressing increase in resistance.

Examples of inorganic particles that may be used include particles of metals (for example, aluminum, iron, or copper), particles of metal oxides (for example, titanium oxide, alumina, zirconium oxide, tin oxide, or zinc oxide), and particles of non-metal oxides (for example, silica). Any one type of inorganic particles listed above may be used or a combination of any two or more types of inorganic particles listed above may be used.

No particular limitations are placed on the intermediate layer resin other than being a resin that can be used to form an intermediate layer. The intermediate layer may contain various additives. Examples of additives that can be added to the intermediate layer resin include the same additives as those listed as examples of the additives used for the photosensitive layer.

<11. Photosensitive Member Production Method>

In a configuration in which the photosensitive member is a multi-layer photosensitive member, the multi-layer photosensitive member is produced as follows, for example. First, an application liquid for charge generating layer formation and an application liquid for charge transport layer formation are prepared. The application liquid for charge generating layer formation is applied onto a conductive substrate and dried to form a charge generating layer. After formation of the charge generating layer, the application liquid for charge transport layer formation is applied onto the charge generating layer and dried to form a charge transport layer. Through the above processes, the multi-layer photosensitive member is produced.

The application liquid for charge generating layer formation is prepared by dissolving or dispersing a charge generating material and optional components (for example, a base resin and various additives), depending on necessity thereof, in a solvent. The application liquid for charge transport layer formation is prepared by dissolving or dispersing a hole transport material and additive components (for example, a binder resin, an electron acceptor compound, and various additives), depending on necessity thereof, in a solvent.

In a configuration in which the photosensitive member is a single-layer photosensitive member, the single-layer photosensitive member is produced as follows, for example. The single-layer photosensitive member is produced by applying an application liquid for single-layer type photosensitive layer formation onto a conductive substrate and drying the application liquid thereon. The application liquid for single-layer type photosensitive layer formation is produced by dissolving or dispersing a charge generating material, a hole transport material, and additive components (for example, an electron transport material, a binder resin, and various additives), depending on necessity thereof, in a solvent.

The solvents contained in the respective application liquids (application liquids for charge generating layer formation, charge transport layer formation, and single-layer type photosensitive layer formation) are not limited particularly as long as they can dissolve or disperse the components contained in the respective application liquids. Specific examples of solvents that can be used include alcohols (for example, methanol, ethanol, isopropanol, or butanol), aliphatic hydrocarbons (for example, n-hexane, octane, or cyclohexane), aromatic hydrocarbons (for example, benzene, toluene, or xylene), halogenated hydrocarbons (for example, dichloromethane, dichloroethane, carbon tetrachloride, or chlorobenzene), ethers (for example, dimethyl ether, diethyl ether, tetrahydrofuran, ethylene glycol dimethyl ether, diethylene glycol dimethyl ether, or propylene glycol monomethyl ether), ketones (for example, acetone, methyl ethyl ketone, or cyclohexanone), esters (for example, ethyl acetate, or methyl acetate), dimethyl formaldehyde, dimethyl formamide, and dimethyl sulfoxide. Any one of the solvents listed above may be used or a combination of any two or more of the solvents listed above may be used. In order to improve workability in production of the photosensitive member, a non-halogenated solvent (i.e., a solvent other than a halogenated hydrocarbon) is preferably used.

Each of the application liquids is prepared by mixing the components in order to disperse the components in the solvent. Mixing or dispersion can be carried out for example using a bead mill, a roll mill, a ball mill, an attritor, a paint shaker, or an ultrasonic disperser.

Each of the application liquids (application liquids for charge generating layer formation, charge transport layer formation, and single-layer type photosensitive layer formation) may contain for example a surfactant in order to improve dispersibility of the components.

A method for applying an application liquid (application liquid for charge generating layer formation, charge transport layer formation, or single-layer type photosensitive layer formation) is not limited particularly as long as the application liquids can be uniformly applied onto or above a conductive substrate. Examples of application methods that may be used include dip coating, spray coating, spin coating, and bar coating.

A method for drying an application liquid (application liquid for charge generating layer formation, charge transport layer formation, or single-layer type photosensitive layer formation) is not limited particularly as long as it can evaporate the solvent in the application liquid. The drying method may for example be heat treatment (hot-air drying) performed using a high-temperature dryer or a reduced pressure dryer. The heat treatment is for example performed for at least 3 minutes and no greater than 120 minutes at a temperature of at least 40° C. and no greater than 150° C.

Note that the photosensitive member production method may involve forming an intermediate layer and/or forming a protective layer depending on necessity thereof. Any known methods are appropriately selected for intermediate layer formation and protective layer formation.

Through the above, the photosensitive member according to the present embodiment has been described. Use of the photosensitive member according to the present embodiment can improve electrical properties of the photosensitive member.

EXAMPLES

The following provides more specific description of the present disclosure through examples. However, note that the present disclosure is not limited to the scope of the examples.

<1. Material of Photosensitive Member>

The following hole transport materials and charge generating materials were prepared as materials for forming charge generating layers and charge transport layers of multi-layer photosensitive members. The following hole transport materials, charge generating materials, and electron transport materials were prepared as materials for forming single-layer type photosensitive layers of single-layer photosensitive members.

<1-1. Hole Transport Material>

The triphenylamine derivatives HT-1-HT-10 described in the first embodiment were prepared as hole transport materials. The triphenylamine derivatives HT-1-HT-10 were each synthesized according to the following methods.

<1-1-1. Synthesis of Compounds 5a, 5b, and 5c>

First, compounds 5a, 5b, and 5c were synthesized as materials used for synthesis of the triphenylamine derivatives HT-1-HT-10, which will be described later. The compound 5a was synthesized according to the following Reactions R-11 and R-12. The compound 5b was synthesized according to the following Reactions R-11 and R-13. The compound 5c was synthesized according to the following Reactions R-11 and R-14.

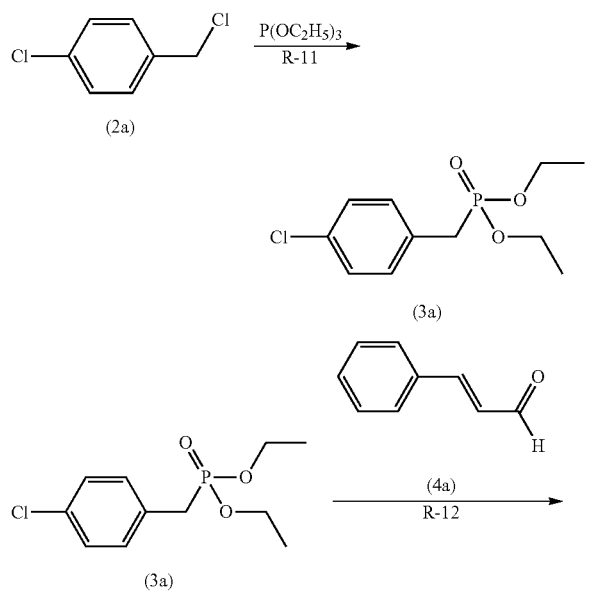

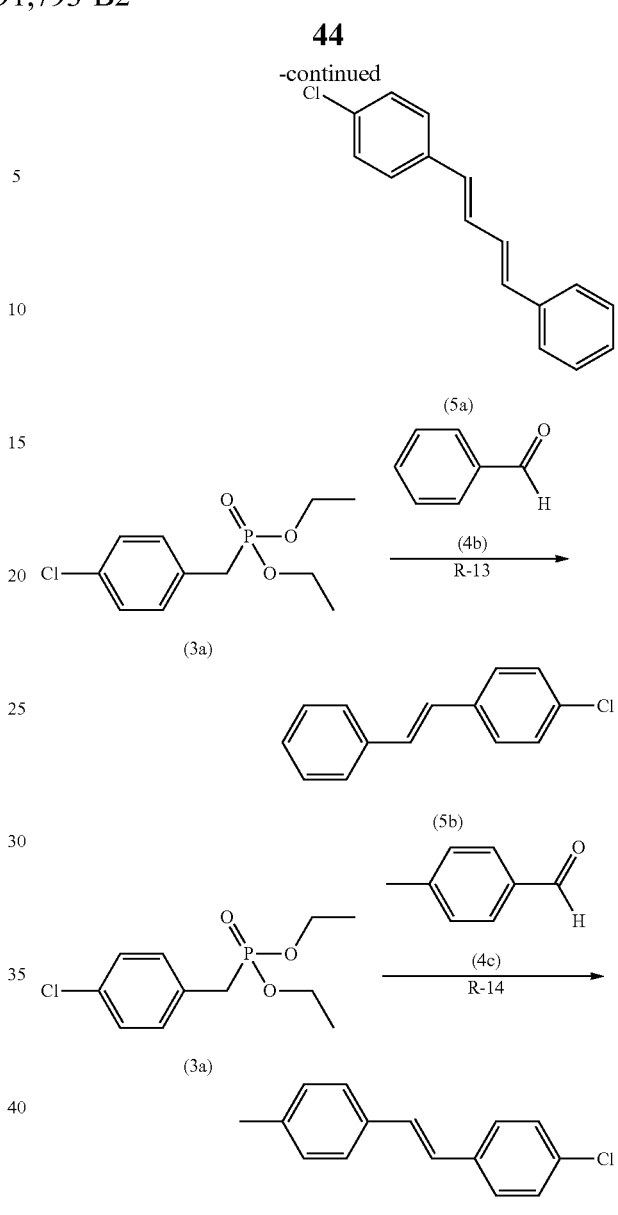

A compound 2a was caused to react with triethyl phosphite in Reaction R-11 to yield a compound 3a. Specifically, a 200 mL flask was charged with the compound 2a (16.1 g, 0.10 moles) and triethyl phosphite (25.0 g, 0.15 moles). The flask contents were stirred for 8 hours at a temperature of 180° C. and then cooled to room temperature. Subsequently, an unreacted triethyl phosphite contained in the flask contents was evaporated under reduced pressure. Through the above processes, a compound 3a in the form of a white liquid was yielded (mass yield 24.1 g, percentage yield 92 mol %).

The compound 3a was caused to react with a compound 4a in Reaction R-12 to yield the compound 5a. Reaction R-12 is a Wittig reaction. Specifically, the compound 3a (13.0 g, 0.05 moles) yielded in Reaction R-11 was added into a 500 mL two-necked flask at a temperature of 0° C. Gas in the flask was replaced with argon gas. Subsequently, dry tetrahydrofuran (100 mL) and 28% sodium methoxide (9.3 g, 0.05 moles) were added into the flask. The flask contents were stirred for 30 minutes. A solution of the compound 4a (7.0 g, 0.05 moles) in dry tetrahydrofuran (300 mL) was then added into the flask. The flask contents were stirred for 12 minutes at room temperature. After pouring the flask contents into ion exchanged water, extraction was performed using toluene. A resultant organic layer was washed five times using ion exchanged water and dried using anhydrous sodium sulfate. A solvent contained in the organic layer was evaporated to leave a residue. The left residue was purified using toluene/methanol (20 mL/100 mL). Through the above processes, the compound 5a in the form of white crystals was yielded (mass yield 9.8 g, percentage yield 80 mol %).

The compound 3a was caused to react with a compound 4a in Reaction R-13 to yield a compound 5b. Reaction R-13 is a Wittig reaction. Reaction R-13 was carried out according to the same method as Reaction R-12 in all aspects other than that the following aspect was altered. The compound 4a (7.0 g, 0.05 moles) in Reaction R-12 was changed to a compound 4b (5.3 g, 0.05 moles). As a result, the compound 5b was yielded (mass yield 8.8 g, percentage yield 85 mol %).

The compound 3a was caused to react with a compound 4c in Reaction R-14 to yield the compound 5c. Reaction R-14 is a Wittig reaction. Reaction R-14 was carried out according to the same method as Reaction R-12 in all aspects other than that the following aspect was altered. The compound 4a (7.0 g, 0.05 moles) in Reaction R-12 was changed to a compound 4c (6.0 g, 0.05 moles). As a result, the compound 5c was yielded (mass yield 9.6 g, percentage yield 88 mol %).

<1-1-2. Synthesis of Compounds 8a and 8b>

Compounds 8a and 8b were synthesized as materials for synthesis of the triphenylamine derivatives HT-1-HT-7, which will be described later. The compound 8a was first synthesized through Reactions R-15, R-16, and R-17.

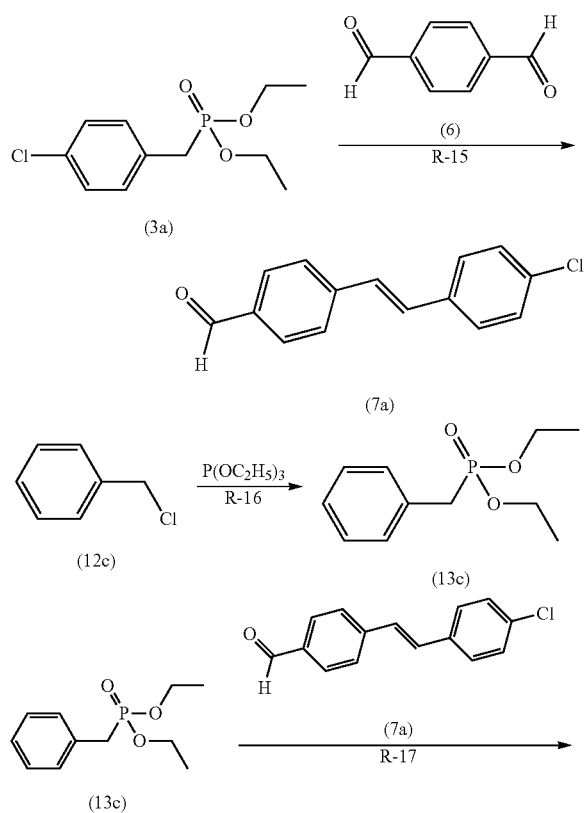

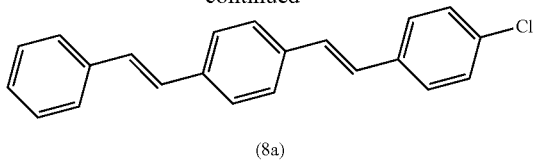

(8a)

The compound 3a was caused to react with a compound 6 in Reaction R-15 to yield a compound 7a. Reaction R-15 is a Wittig reaction. Specifically, the compound 3a (13.0 g. 0.05 moles) resulting from Reaction R-11 was added into a 500 mL two-necked flask at a temperature of 0° C. Gas in the flask was replaced with argon gas. A dry tetrahydrofuran (100 mL) and a solution of the compound 6 (35.0 g, 0.27 moles) in dry tetrahydrofuran (300 mL) was then added into the flask. The flask contents were stirred for 30 minutes. Next, 28% sodium methoxide (9.3 g, 0.05 moles) was added into the flask. The flask contents were stirred for 12 hours at room temperature. After pouring the flask contents into ion exchanged water, extraction was performed using toluene. A resultant organic layer was washed five times using ion exchanged water and dried using anhydrous sodium sulfate. A solvent contained in the organic layer was then evaporated to leave a residue. The left residue was purified using toluene/methanol (20 mL/100 mL). Through the above processes, a compound 7a in the form of white crystals was yielded (mass yield 3.6 g, percentage yield 30 mol %).

A compound 12c was caused to react with triethyl phosphite in Reaction R-16 to yield a compound 13c. Specifically, a 200 mL flask was charged with the compound 12c (12.7 g, 0.10 moles) and triethyl phosphite (25.0 g, 0.15 moles). After being stirred for 8 hours at a temperature of 180° C., the flask contents were cooled to room temperature. Subsequently, unreacted triethyl phosphite contained in the flask contents was evaporated under reduced pressure. Through the above processes, the compound 13c in the form of a white liquid was yielded (mass yield 21.3 g, percentage yield 93 mol %).

The compound 13c was caused to react with the compound 7a in Reaction R-17 to yield the compound 8a. Reaction R-17 is a Wittig reaction. Specifically, the compound 13c (11.4 g, 0.05 moles) resulting from Reaction R-16 was added into a 500 mL two-necked flask at a temperature of 0° C. Gas in the flask was replaced with argon gas. Dry tetrahydrofuran (100 mL) and 28% sodium methoxide (9.3 g, 0.05 moles) were then added into the flask. The flask contents were stirred for 30 minutes. A solution of the compound 7a (12.2 g, 0.05 moles), which has resulted from Reaction R-15, in dry tetrahydrofuran solution (300 mL) was added into the flask then. The flask contents were stirred for 12 hours at room temperature. After pouring the flask contents into ion exchanged water, extraction was performed using toluene. A resultant organic layer was washed five times using ion exchanged water and dried using anhydrous sodium sulfate. A solvent contained in the organic layer was then evaporated to leave a residue. The left residue was purified using toluene/methanol (20 mL/100 mL). Through the above processes, the compound 8a in the form of a white liquid was yielded (mass yield 14.0 g, percentage yield 88 mol %).

The compound 8b was then synthesized according to the following Reactions R-18 and R-19.

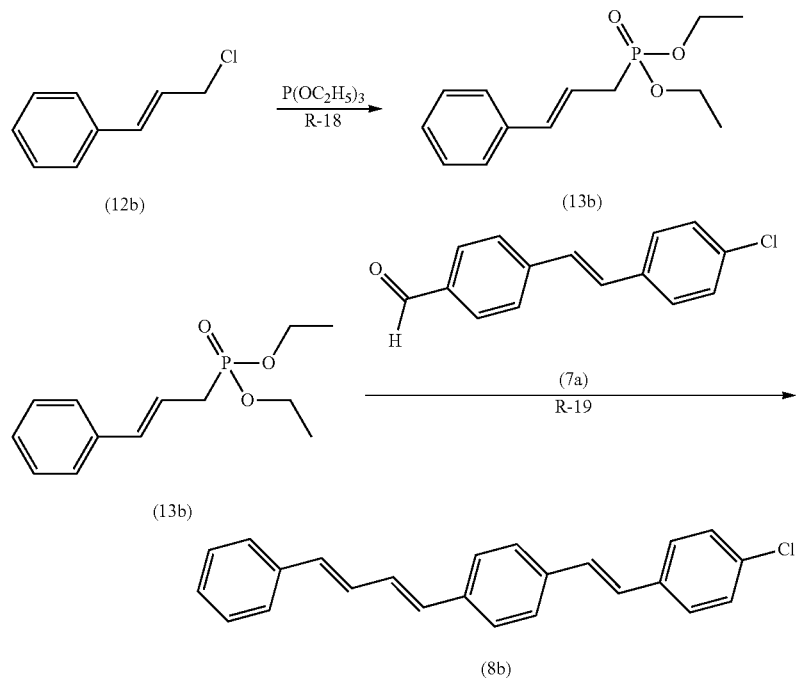

A compound 12b was caused to react with triethyl phosphite in Reaction R-18 to yield a compound 13b. Specifically, a 200 mL flask was charged with the compound 12b (15.2 g, 0.10 moles) and triethyl phosphite (25.0 g, 0.15 moles). After being stirred for 8 hours at a temperature of 180° C., the flask contents were cooled to room temperature. Subsequently, unreacted triethyl phosphite contained in the flask contents was evaporated under reduced pressure. Through the above processes, the compound 13b in the form of a white liquid was yielded (mass yield 23.5 g, percentage yield 92 mol %).

The compound 13b was caused to react with the compound 7a in Reaction R-19 to yield the compound 8b. Reaction R-19 is a Wittig reaction. Reaction R-19 was carried out according to the same method as Reaction R-17 in all aspects other than that the following aspect was altered. The compound 13c (11.4 g, 0.050 moles) in Reaction R-17 was changed to the compound 13b (12.8 g, 0.050 moles). As a result, the compound 8b was yielded (mass yield 15.3 g, percentage yield 89 mol %).

<1-1-3. Synthesis of Triphenylamine Derivative HT-1>

The triphenylamine derivative HT-1 was synthesized next according to the following Reaction R-20.

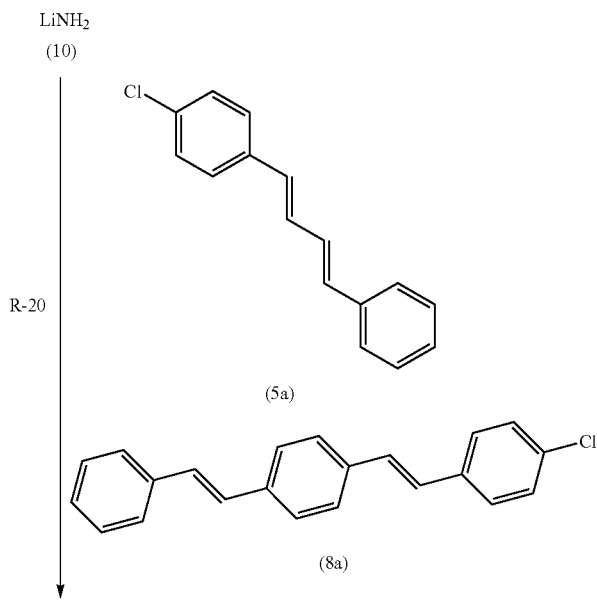

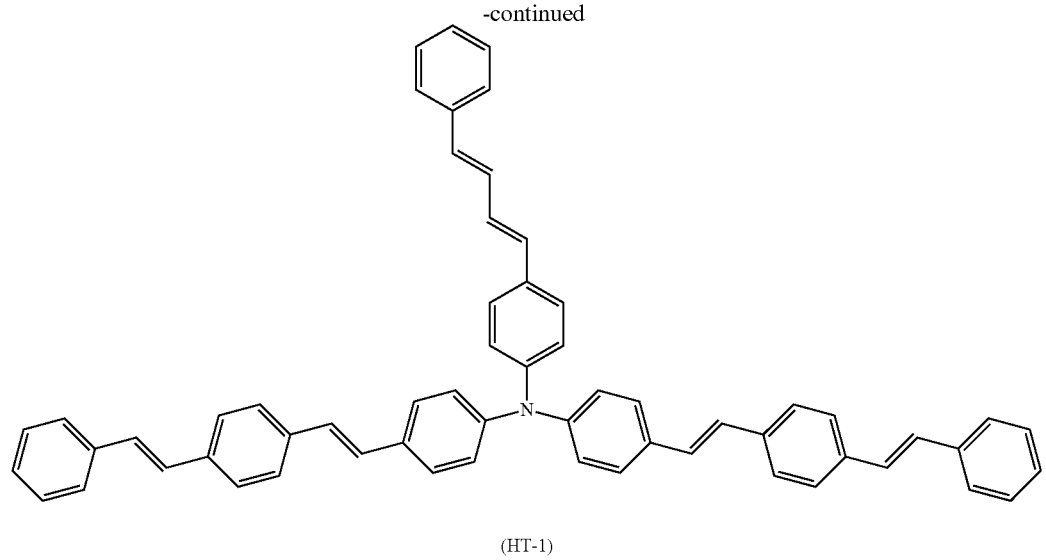

(HT-1)

In Reaction R-20, a compound 10 was caused to react with the compounds 5a and 8a to produce the triphenylamine derivative HT-1. Reaction R-20 is a coupling reaction. Specifically, a three-necked flask was charged with the compound 8a (6.3 g, 0.020 moles, a second material indicated in Table 1), the compound 5a (2.5 g, 0.010 moles, a first material indicated in Table 1), tricyclohexylphosphine (0.105 g, 0.000300 moles), tris(dibenzylideneacetone)dipalladium(0) (0.137 g, 0.000150 moles), sodium tert-butoxide (4.0 g, 0.042 moles), the compound 10 (lithium amide, 0.24 g, 0.010 moles), and distilled o-xylene (300 mL). Gas in the flask was replaced with argon gas. After being stirred for 5 hours at a temperature of 120° C., the flask contents were then cooled to room temperature. The flask contents were washed three times using ion exchanged water, thereby obtaining an organic layer. Anhydrous sodium sulfate and activated clay were added to the organic layer in order to perform drying treatment and adsorption treatment. Subsequently, the organic layer subjected to the drying treatment and the adsorption treatment was evaporated under reduced pressure, thereby removing o-xylene. Through the above, a residue was left. The left residue was purified according to silica gel chromatography using chloroform/hexane (volume ratio 1:1) as a developing solvent. As a result, the triphenylamine derivative HT-1 was produced (mass yield 5.6 g, percentage yield 69 mol %).

<1-1-4. Synthesis of Triphenylamine Derivatives HT-2-HT-4, HT-9, and HT-10>

The triphenylamine derivatives HT-2-HT-4, HT-9, and HT-10 were synthesized according to the same method as that for synthesis of the triphenylamine derivative HT-1 in all aspects other than that the following aspects were altered.

The first material used in Reaction R-20 was changed from the compound 5a (2.5 g, 0.010 moles) used in synthesis of the triphenylamine derivative HT-1 to respective first materials (the compounds 5a, 5b, and 5c) indicated in Table 1, and the amount thereof was changed to those indicated in Table 1. The second material used in Reaction R-20 was changed from the compound 8a (6.3 g, 0.020 moles) used in synthesis of the triphenylamine derivative HT-1 to respective second materials (the compounds 8a or 8b) indicated in Table 1, and the amount thereof was changed to those indicated in Table 1. As a result, reaction products indicated in Table 1 (triphenylamine derivatives HT-2-HT-4, TH-9, and HT-10) were produced in Reaction R-20 instead of the triphenylamine derivative HT-1. The mass yields and the percentage yields of the respective reaction products resulting from Reaction R-20 are indicated in Table 1.

In Table 1, the compounds 5a-5c, 8a, and 8b are represented by the following chemical formulas (5a)-(5c), (8a), and (8b), respectively. Note that the compounds 5a-5c, 8a, and 8b were yielded through Reactions R-12-R14, R-17, and R-19.

TABLE 1

| | Reaction R-21 | | | | | | | |
|---|---|---|---|---|---|---|---|---|
| | First material | | | Second material | | | Reaction product | | |
| Compound | Additive amount [g] | Additive amount [mol] | Compound | Additive amount [g] | Additive amount [mol] | Triphenylamine Derivative | Mass yield [g] | Percentage yield [mol %] |
| 5a | 2.5 | 0.010 | 8a | 6.3 | 0.020 | HT-1 | 5.6 | 69 |
| 5a | 2.4 | 0.010 | 8b | 6.9 | 0.020 | HT-2 | 5.4 | 62 |
| 5c | 2.3 | 0.010 | 8a | 6.3 | 0.020 | HT-3 | 5.8 | 72 |
| 5b | 2.1 | 0.010 | 8b | 6.9 | 0.020 | HT-4 | 5.7 | 68 |

TABLE 1-continued

| Reaction R-21 | | | | | | | | |
|---|---|---|---|---|---|---|---|---|
| First material | | | Second material | | | Reaction product | | |
| Compound | Additive amount [g] | Additive amount [mol] | Compound | Additive amount [g] | Additive amount [mol] | Triphenylamine Derivative | Mass yield [g] | Percentage yield [mol %] |
| None | None | None | 8b | 10.3 | 0.030 | HT-9 | 4.8 | 49 |
| 5a | 4.8 | 0.020 | 8b | 3.4 | 0.010 | HT-10 | 4.6 | 60 |

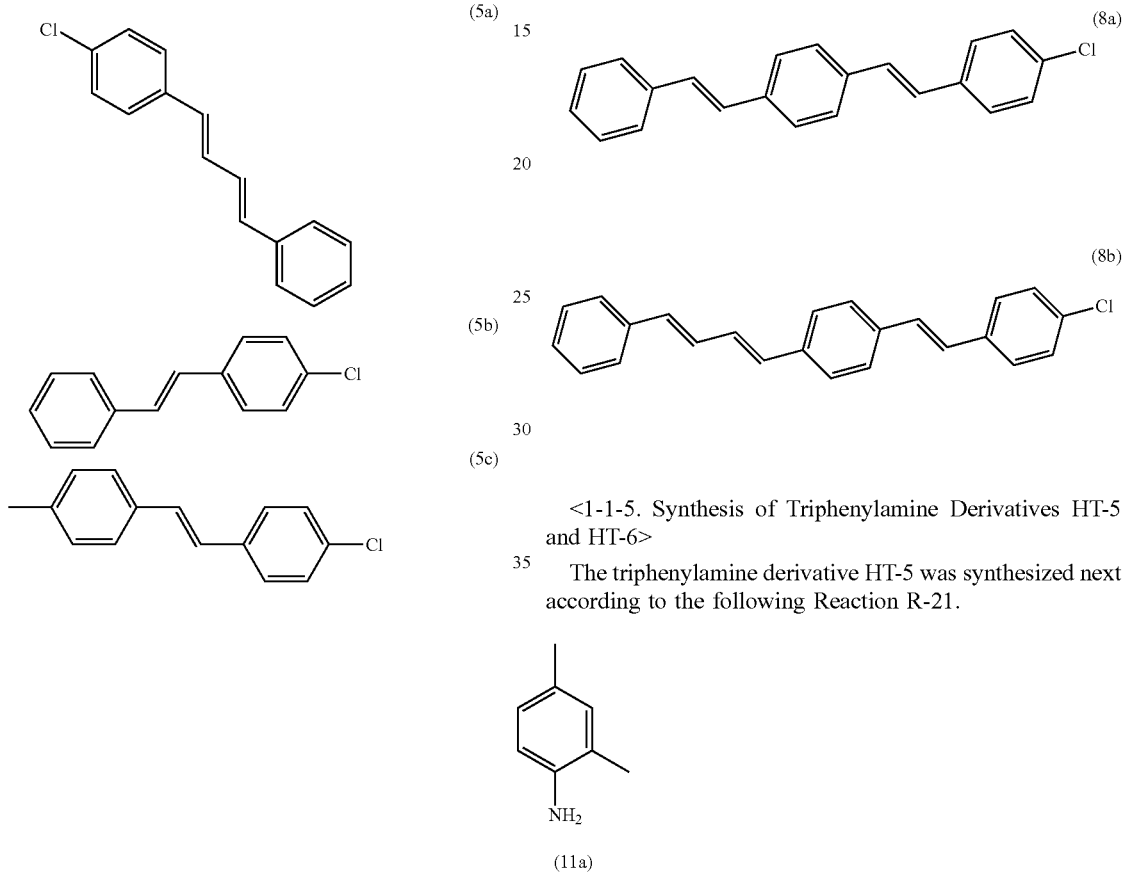

<1-1-5. Synthesis of Triphenylamine Derivatives HT-5 and HT-6>

The triphenylamine derivative HT-5 was synthesized next according to the following Reaction R-21.

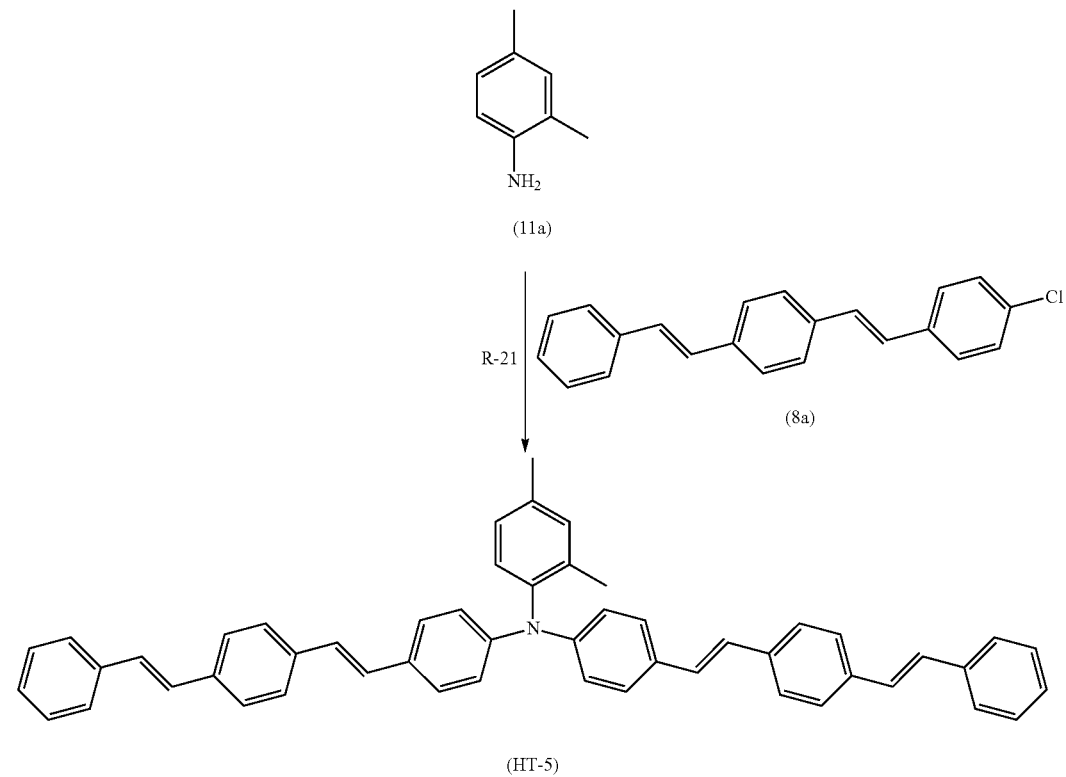

In Reaction R-21, a compound 11a was caused to react with the compound 8a to produce the triphenylamine derivative HT-5. Reaction R-21 is a coupling reaction. Specifically, a three-necked flask was charged with the compound 8a (9.5 g, 0.030 moles), tricyclohexylphosphine (0.105 g, 0.000300 moles) tris(dibenzylideneacetone)dipalladium(0) (0.137 g, 0.000150 moles), sodium tert-butoxide (4.0 g, 0.042 moles), the compound 11a (1.8 g, 0.015 moles), and distilled o-xylene (300 mL). Note that compound 8a was yielded through Reaction R-17. Gas in the flask was replaced with argon gas. After being stirred for 5 hours at a temperature of 120° C., the flask contents were then cooled to room temperature. The flask contents were washed three times using ion exchanged water, thereby obtaining an organic layer. Anhydrous sodium sulfate and activated clay were added to the organic layer in order to perform drying treatment and adsorption treatment. Subsequently, the organic layer subjected to the drying treatment and the adsorption treatment was evaporated under reduced pressure, thereby removing o-xylene. Through the above, a residue was left. The left residue was purified according to silica gel chromatography using chloroform/hexane (volume ratio 1:1) as a developing solvent. Through the above processes, the triphenylamine derivative HT-5 was produced (mass yield 7.5 g, percentage yield 75 mol %).

The triphenylamine derivative HT-6 was then synthesized according to the same method as that for synthesis of the triphenylamine derivative HT-5 in all aspects other than that the following aspects were altered. For use in Reaction R-21, the compound 11a (1.8 g, 0.015 moles) used in synthesis of the triphenylamine derivative HT-5 was changed to the following compound 11b (1.6 g, 0.015 moles). Also, for use in Reaction R-21, the compound 8a (9.5 g, 0.030 moles) used in synthesis of the triphenylamine derivative HT-5 was changed to the compound 8b (10.3 g, 0.030 moles). Note that the compound 8b was yielded through Reaction R-19. As a result, the triphenylamine derivative HT-6 (mass yield 7.8 g, percentage yield 71%) was produced in Reaction R-21 instead of the triphenylamine derivative HT-5.

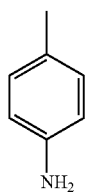

(11b)

<1-1-6. Synthesis of Triphenylamine Derivatives HT-7 and HT-8>

The triphenylamine derivative HT-7 was next synthesized according to the following Reaction R-22.

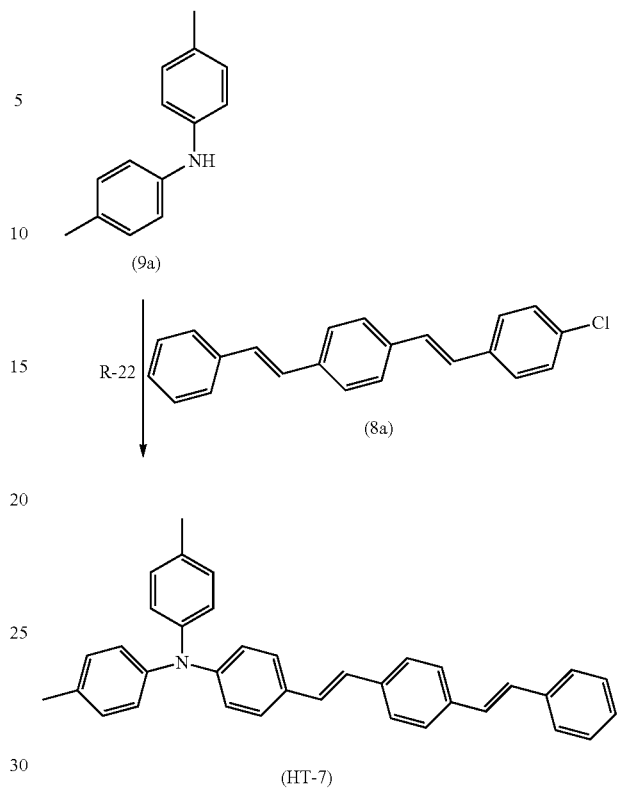

In Reaction R-22, a compound 9a was caused to react with the compound 8a to produce the triphenylamine derivative HT-7. Reaction R-22 is a coupling reaction. Specifically, a three-necked flask was charged with the compound 8a (4.8 g, 0.015 moles), tricyclohexylphosphine (0.105 g, 0.000300 moles), tris(dibenzylideneacetone)dipalladium(0) (0.137 g, 0.000150 moles), sodium tert-butoxide (4.0 g, 0.042 moles), the compound 9a (3.0 g, 0.015 moles), and distilled o-xylene (300 mL). Note that compound 8a was yielded through Reaction R-17. Gas in the flask was replaced with argon gas. After being stirred for 5 hours at a temperature of 120° C., the flask contents were cooled to room temperature. The flask contents were washed three times using ion exchanged water, thereby obtaining an organic layer. Anhydrous sodium sulfate and activated clay were added to the organic layer in order to perform drying treatment and adsorption treatment. Subsequently, the organic layer subjected to the drying treatment and the adsorption treatment was evaporated under reduced pressure, thereby removing o-xylene. Through the above, a residue was left. The left residue was purified according to silica gel chromatography using chloroform/hexane (volume ratio 1:1) as a developing solvent. As a result, the triphenylamine derivative HT-7 was produced (mass yield 5.6 g, percentage yield 78 mol %).

The triphenylamine derivative HT-8 was then synthesized according to the same method as that for synthesis of the triphenylamine derivative HT-7 in all aspect other than that the following aspect was altered. For use in Reaction R-22, the compound 8a (4.8 g, 0.015 moles) used in synthesis of the triphenylamine derivative HT-7 was changed to the compound 8b (5.1 g, 0.015 moles). Note that the compound 8b was yielded through Reaction R-19. As a result, the triphenylamine derivative HT-8 (mass yield 6.1 g, percentage yield 81%) was produced in Reaction R-22 instead of the triphenylamine derivative HT-7.

Figure 2:
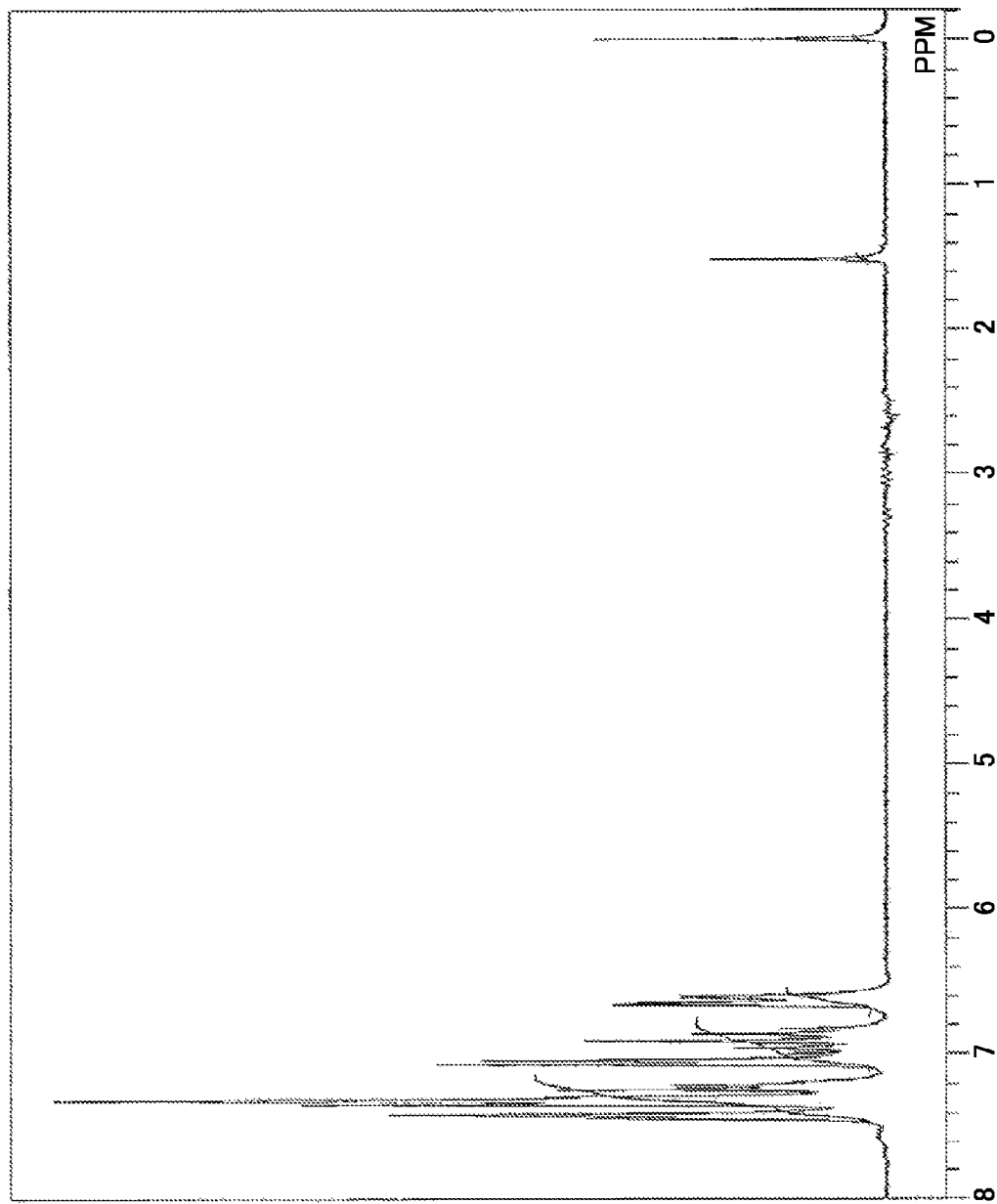
FIG. 2 shows a $^1$H-NMR spectrum of a triphenylamine derivative represented by chemical formula (HT-2) according to the first embodiment of the present disclosure.
Figure 3:
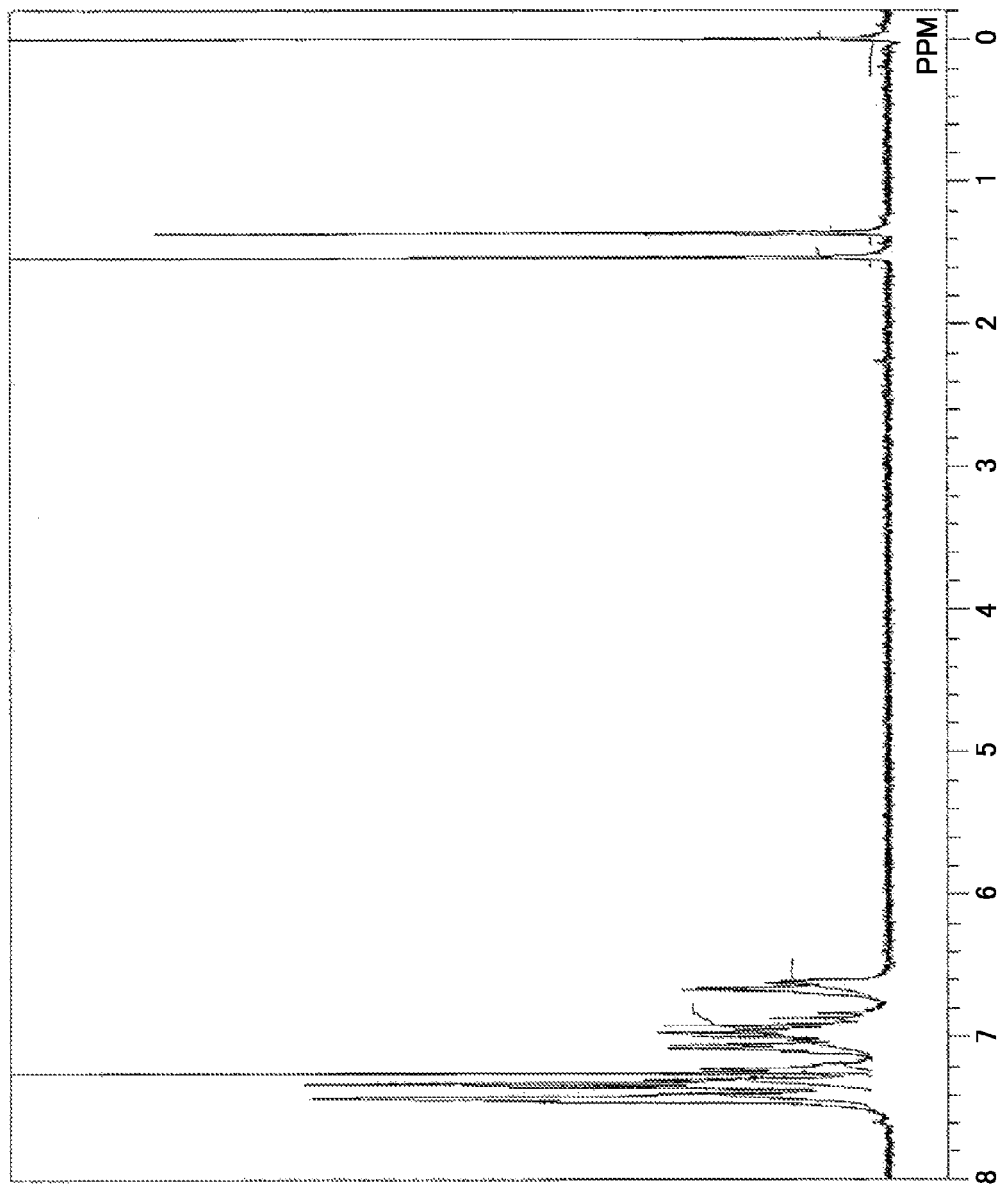
FIG. 3 shows a $^1$H-NMR spectrum of a triphenylamine derivative represented by chemical formula (HT-10) according to the first embodiment of the present disclosure.

Subsequently, the synthesized triphenylamine derivatives HT-1, HT-2, and HT-10 were each analyzed using $^1$H-NMR (a proton nuclear magnetic resonance spectrometer). The magnetic field intensity of the proton nuclear magnetic resonance spectrometer was set to 300 MHz. Deuterated chloroform ($CDCl_3$) was used as a solvent. Tetramethylsilane (TMS) was used as an internal standard material. For the triphenylamine derivative HT-1, a measured $^1$H-NMR spectrum is indicated in FIG. 1 and chemical shift values thereof are indicated below. For the triphenylamine derivative HT-2, a measured $^1$H-NMR spectrum is indicated in FIG. 2 and chemical shift values thereof are indicated below. For the triphenylamine derivative HT-10, a measured $^1$H-NMR spectrum is indicated in FIG. 3 and chemical shift values thereof are indicated below. It was confirmed from the $^1$H-NMR spectra and the chemical shift values that the triphenylamine derivatives HT-1, HT-2, and HT-10 have structures represented by chemical formulas (HT-1), (HT-2), and (HT-10), respectively.

Triphenylamine derivative HT-1: $^1$H-NMR (300 MHz, $CDCl_3$) δ 6.6-6.7 (m, 8H), 6.8-7.1 (m, 16H), 7.2-7.5 (m, 23H).

Triphenylamine derivative HT-2: $^1$H-NMR (300 MHz, $CDCl_3$) δ 6.6-6.7 (m, 8H), 6.8-7.1 (m, 16H), 7.2-7.5 (m, 27H).

Triphenylamine derivative HT-10: $^1$H-NMR (300 MHz, $CDCl_3$) δ 6.6-6.7 (m, 6H), 6.8-7.1 (m, 14H), 7.2-7.5 (m, 25H).

<1-1-7. Preparation of Triphenylamine Derivatives HT-A-HT-C>

Triphenylamine derivatives represented by the following chemical formulas (HT-A)-(HT-C) were also prepared. Hereinafter, the triphenylamine derivative represented by chemical formulas (HT-A)-(HT-C) may be referred to as triphenylamine derivatives HT-A-HT-C, respectively.

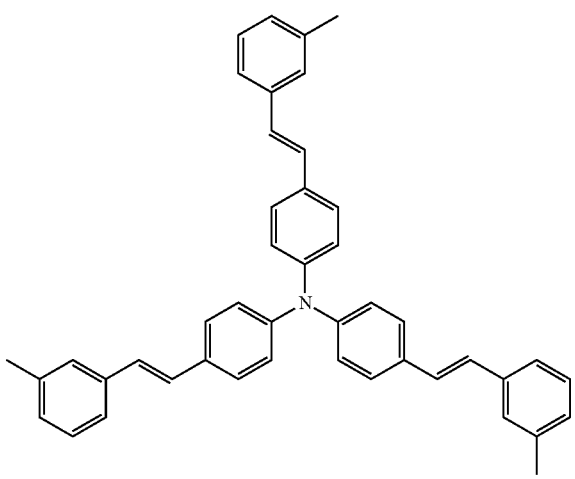
(HT-A)

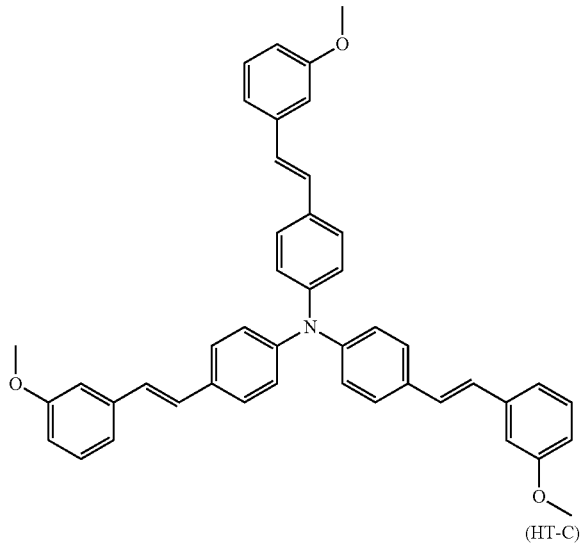
(HT-B)

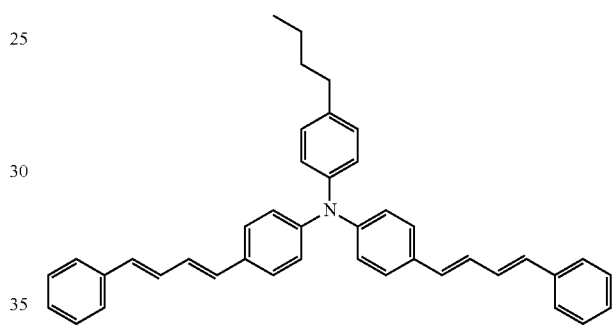
(HT-C)

<1-2. Charge Generating Material>

For charge generating materials, compounds CG-1X and CG-2Y were prepared. The compound CG-1X was a metal-free phthalocyanine represented by chemical formula (CG-1) described in the second embodiment. The compound CG-1X had a crystal structure of X-form.

The compound CG-2Y was a titanyl phthalocyanine represented by chemical formula (CG-2) described in the second embodiment. The compound CG-2Y had a crystal structure of Y-form.

<1-3. Electron Transport Material>

The compounds ET-1 and ET-4 described in the second embodiment were prepared for electron transport materials to be contained in the single-layer type photosensitive layer of the single-layer photosensitive member.

<2. Multi-Layer Photosensitive Member Production>

Multi-layer photosensitive members A-1-A-10 and B-1-B-3 were produced using the above described materials for photosensitive layer formation.

<2-1. Production of Multi-Layer Photosensitive Member A-1>

First, surface treated titanium oxide (test sample SMT-02 produced by Tayca Corporation, number average primary particle size 10 nm) was prepared. The surface treated titanium oxide was prepared as follows. Titanium oxide was surface treated using alumina and silica. After being subjected to the above surface treatment using alumina and silica, the titanium oxide was further surface treated using methyl hydrogen polysiloxane during wet dispersion.

Next, an application liquid for undercoat layer formation was prepared. Specifically, a vessel was charged with the surface treated titanium oxide (2.8 parts by mass), a copolyamide resin (DAIAMID X4685 produced by Daicel-Evonik Ltd., 1 part by mass), ethanol (10 parts by mass) as a solvent, and butanol (2 parts by mass) as a solvent. Mixing was performed on the vessel contents for 5 hours using a bead mill in order to disperse the materials in the solvent. Through the above, an application liquid for undercoat layer formation was obtained.

Subsequently, an undercoat layer was formed. Specifically, the resultant application liquid for undercoat layer formation was filtered using a filter having a pore size of 5 μm. After the filtration, the application liquid for undercoat layer formation was applied onto the surface of a conductive substrate—an aluminum drum-shaped support (diameter 30 mm, total length 238.5 mm)—by dip coating. The applied application liquid for undercoat layer formation was heated for 30 minutes at a temperature of 130° C. Through the above processes, an undercoat layer (film thickness 1.5 μm) was formed on the conductive substrate.

Next, an application liquid for charge generating layer formation was prepared. Specifically, a vessel was charged with the compound CG-2Y (1 part by mass) as a charge generating material, a polyvinyl butyral resin (Denka Butyra #6000EP produced by Denka Company Limited, 1 part by mass) as a base resin, propylene glycol monomethyl ether (40 parts by mass) as a dispersion medium, and tetrahydrofuran (40 parts by mass) as a dispersion medium. The vessel contents were mixed for 2 hours using a bead mill in order to disperse the materials in the solvent. Through the above, an application liquid for charge generating layer formation was obtained. The resultant application liquid for charge generating layer formation was then filtered using a filter having a pore size of 3 μm. The application liquid for charge generating layer formation was then applied by dip coating onto the conductive substrate on which the undercoat layer was formed. Next, the applied application liquid for charge generating layer formation was dried for 5 minutes at a temperature of 50° C. Through the above processes, a charge generating layer having a thickness of 0.3 μm was formed on the undercoat layer.

Next, an application liquid for charge transport layer formation was prepared. Specifically, a vessel was charged with the triphenylamine derivative HT-1 (70 parts by mass) as a hole transport material, a bisphenol Z-type polycarbonate resin (Panlite (registered Japanese trademark) TS-2050 produced by Teijin Limited, viscosity average molecular weight 50,000, 100 parts by mass) as a binder resin, di(tert-butyl)p-cresol (BHT, 5 parts by mass) as an additive, tetrahydrofuran (430 parts by mass) as a solvent, and toluene (430 parts by mass) as a solvent. The vessel contents were mixed to dissolve the materials in a solvent of the tetrahydrafuran and the toluene. Through the above, an application liquid for charge transport layer formation was obtained. Subsequently, the resultant application liquid for charge transport layer formation was applied according to the same manner as that for the application liquid for charge generating layer formation onto the conductive substrate on which the undercoat layer and the charge generating layer were formed. The applied application liquid for charge transport layer formation was dried for 30 minutes at a temperature of 130° C. Through the above processes, a charge transport layer having a thickness of 2.0 μm was formed on the charge generating layer. The multi-layer photosensitive member A-1 was produced as a result of the processes described above.

<2-2. Production of multi-layer photosensitive members A-2-A-10 and B-1-B-3>

Multi-layer photosensitive members A-2-A-10 and B-1-B-3 were produced by the same method as that for the multi-layer photosensitive member A-1 in all aspects other the following aspect was altered. The triphenylamine derivative HT-1 as a hole transport material used in production of the multi-layer photosensitive member A-1 was changed to hole transport materials indicated in Table 2.

<3. Single-Layer Photosensitive Member Production>

Single-layer photosensitive members C-1-C-18 and D-1-D-9 were produced using materials for photosensitive layer formation.

<3-1. Production of Single-layer Photosensitive Member C-1>

A vessel was charged with the compound CG-1X (5 parts by mass) as a charge generating material, the triphenylamine derivative HT-1 (80 parts by mass) as a hole transport material, the compound ET-1 (50 parts by mass) as an electron transport material, a bisphenol Z-type polycarbonate (Panlite (registered Japanese trademark) TS-2050 produced by Teijin Limited, viscosity average molecular weight 50,000, 100 parts by mass) as a binder resin, and tetrahydrofuran (800 parts by mass) as a solvent. The vessel contents were mixed for 50 hours using a ball mill in order to disperse the materials in the solvent. Through the above processes, an application liquid for single-layer type photosensitive layer formation was obtained. The application liquid for single-layer type photosensitive layer formation was applied onto a conductive substrate—an aluminum drum-shaped support (diameter 30 mm, total length 238.5 mm)—by dip coating. The applied application liquid for single-layer type photosensitive layer formation was dried for 30 minutes at a temperature of 100° C. Through the above processes, a single-layer type photosensitive layer having a film thickness of 25 μm was formed on the conductive substrate. The single-layer photosensitive member C-1 was produced as a result of the processes described above.

<3-2. Production of Single-layer Photosensitive Members C-2-C18 and D-1-D-9>

The single-layer photosensitive members C-2-C18 and D-1-D-9 were produced according to the same method as that for the single-layer photosensitive member C-1 in all aspects other than the following points were altered. The compound CG-1X used as a charge generating material in production of the single-layer photosensitive member C-1 was changed to charge generating materials indicated in Tables 3. The triphenylamine derivative HT-1 as a hole transport material used in production of the single-layer photosensitive member C-1 was changed to hole transport materials indicated in Table 3. The compound ET-1 used as an electron transport material in production of the single-layer photosensitive member C-1 was changed to electron transport materials indicated in Tables 3.

<4. Evaluation of Multi-Layer Photosensitive Member Electrical Properties>

Electric properties of each of the produced multi-layer photosensitive members A-1-A-10 and B-1-B-3 were evaluated. Evaluation of electric properties was performed in an environment at a temperature of 2° C. and at a humidity of 60% RH. First, the surface of the multi-layer photosensitive member was negatively charged using a drum sensitivity test device (product of Gen-Tech, Inc.). The surface of the multi-layer photosensitive member was charged under conditions of a photosensitive drum rotation speed of 31 rpm and an inflow current to the multi-layer photosensitive member of −8 µA. The surface potential of the multi-layer photosensitive member was measured directly after the charging. The measured surface potential of the multi-layer photosensitive member was taken to be an initial surface potential ($V_0$, units: V). Subsequently, monochromatic light (wavelength 780 nm, half-width 20 nm, optical energy 0.4 µJ/cm$^2$) was taken out from white light of a halogen lamp using a bandpass filter. The surface of the multi-layer photosensitive member was irradiated with the taken monochromatic light. The surface potential of the multi-layer photosensitive member was measured once 0.5 seconds had elapsed after completion of the irradiation. The measured surface potential was taken to be a residual potential ($V_L$, units: V). Initial surface potentials ($V_0$) and residual potentials ($V_L$) of the multi-layer photosensitive members that were measured are shown in Table 2. It should be noted that a residual potential ($V_L$) having a smaller absolute value indicates better electrical properties.

<5. Evaluation of Single-Layer Photosensitive Member Electrical Properties>

Evaluation of electric properties was performed on each of the single-layer photosensitive members C-1-C-18 and D-1-D-9 produced as above. Evaluation of electric properties was performed in an environment at a temperature of 23° C. and at a humidity of 60% RH. First, the surface of the single-layer photosensitive member was positively charged using a drum sensitivity test device (product of Gen-Tech, Inc.). The surface of the single-layer photosensitive member was charged under conditions of a photosensitive drum rotation speed of 31 rpm and an inflow current to the single-layer photosensitive member of +8 µA. The surface potential of the single-layer photosensitive member was measured directly after the charging. The measured surface potential of the single-layer photosensitive member was taken to be an initial surface potential ($V_0$, units: V). Subsequently, monochromatic light (wavelength 780 nm, half-width 20 nm, optical energy 1.5 µJ/cm$^2$) was taken out from white light of a halogen lamp using a bandpass filter. The surface of the single-layer photosensitive member was irradiated with the taken monochromatic light. The surface potential of the single-layer photosensitive member was measured once 0.5 seconds had elapsed after completion of the irradiation. The measured surface potential was taken to be a residual potential ($V_L$, units: V). Initial surface potentials ($V_0$) and residual potentials ($V_L$) of the single-layer photosensitive members that were measured are shown in Table 3. It should be noted that a residual potential ($V_L$) having a smaller absolute value indicates better electrical properties.

<6. Evaluation of Resistance to Crystallization>

The entire region of the surface (photosensitive layer) of each of the multi-layer photosensitive members A-1-A-10 and B-1-B-3 and the single-layer photosensitive members C-1-C-8 and D-1-D-9 was visually observed. Through the above observation, it was confirmed whether or not a crystallized portion was present at the surface of the photosensitive member. Based on the results of the above confirmation, the external appearance of each of the multi-layer photosensitive members and single-layer photosensitive members was evaluated in terms of resistance to crystallization in accordance with the following evaluation standard. The results of the evaluation of resistance to crystallization are indicated in Tables 2 and 3.

(Evaluation Standard of Resistance to Crystallization)
Good: No crystallized portion observed
Mediocre: Crystallized portion partly observed
Poor: Crystallized portion observed Evaluation results of electric properties and resistance to crystallization for the multi-layer photosensitive members are indicated in Table 2. Evaluation results of electric properties and resistance to crystallization for the single-layer photosensitive members are indicated in Table 3. In Tables 2 and 3, CGM, HTM, ETM, $V_0$, and $V_L$ represent a charge generating material, a hole transport material, an electron transport material, initial potential, and residual potential, respectively.

TABLE 2

| | Multi-layer photosensitive member | HTM | Electrical properties $V_0$ (V) | $V_L$ (V) | Resistance to crystallization Evaluation |
|---|---|---|---|---|---|
| Example 1 | A-1 | HT-1 | −700 | −89 | Excellent |
| Example 2 | A-2 | HT-2 | −700 | −85 | Excellent |
| Example 3 | A-3 | HT-3 | −700 | −95 | Excellent |
| Example 4 | A-4 | HT-4 | −700 | −93 | Excellent |
| Example 5 | A-5 | HT-5 | −700 | −102 | Mediocre |
| Example 6 | A-6 | HT-6 | −700 | −100 | Excellent |
| Example 7 | A-7 | HT-7 | −700 | −111 | Excellent |
| Example 8 | A-8 | HT-8 | −700 | −108 | Excellent |
| Example 9 | A-9 | HT-9 | −700 | −87 | Mediocre |
| Example 10 | A-10 | HT-10 | −700 | −93 | Excellent |
| Comparative Example 1 | B-1 | HT-A | −700 | −125 | Excellent |
| Comparative Example 2 | B-2 | HT-B | −700 | −123 | Excellent |
| Comparative Example 3 | B-3 | HT-C | −700 | −115 | Excellent |

TABLE 3

| | Single-layer photosensitive member | CGM | HTM | ETM | Electrical properties $V_0$ (V) | $V_L$ (V) | Resistance to crystallization Evaluation |
|---|---|---|---|---|---|---|---|
| Example 11 | C-1 | CG-1X | HT-1 | ET-1 | +700 | +98 | Excellent |
| Example 12 | C-2 | CG-1X | HT-1 | ET-4 | +699 | +97 | Excellent |
| Example 13 | C-3 | CG-2Y | HT-1 | ET-4 | +700 | +93 | Excellent |
| Example 14 | C-4 | CG-1X | HT-2 | ET-1 | +698 | +100 | Excellent |
| Example 15 | C-5 | CG-1X | HT-2 | ET-4 | +700 | +97 | Excellent |
| Example 16 | C-6 | CG-2Y | HT-2 | ET-4 | +700 | +92 | Excellent |
| Example 17 | C-7 | CG-1X | HT-4 | ET-1 | +700 | +103 | Excellent |
| Example 18 | C-8 | CG-1X | HT-4 | ET-4 | +699 | +104 | Excellent |
| Example 19 | C-9 | CG-2Y | HT-4 | ET-4 | +700 | +100 | Excellent |
| Example 20 | C-10 | CG-1X | HT-6 | ET-1 | +700 | +110 | Mediocre |
| Example 21 | C-11 | CG-1X | HT-6 | ET-4 | +699 | +109 | Mediocre |
| Example 22 | C-12 | CG-2Y | HT-6 | ET-4 | +699 | +106 | Mediocre |

TABLE 3-continued

| Single-layer photosensitive member | | CGM | HTM | ETM | Electrical properties | | Resistance to crystallization Evaluation |
| --- | --- | --- | --- | --- | --- | --- | --- |
| | | | | | $V_0$ (V) | $V_L$ (V) | |
| Example 23 | C-13 | CG-1X | HT-8 | ET-1 | +700 | +106 | Excellent |
| Example 24 | C-14 | CG-1X | HT-8 | ET-4 | +699 | +105 | Excellent |
| Example 25 | C-15 | CG-2Y | HT-8 | ET-4 | +700 | +101 | Excellent |
| Example 26 | C-16 | CG-1X | HT-10 | ET-1 | +700 | +100 | Mediocre |
| Example 27 | C-17 | CG-1X | HT-10 | ET-4 | +699 | +98 | Mediocre |
| Example 28 | C-18 | CG-2Y | HT-10 | ET-4 | +699 | +94 | Mediocre |
| Comparative Example 4 | D-1 | CG-1X | HT-A | ET-1 | +699 | +125 | Mediocre |
| Comparative Example 5 | D-2 | CG-1X | HT-A | ET-4 | +700 | +122 | Mediocre |
| Comparative Example 6 | D-3 | CG-2Y | HT-A | ET-4 | +701 | +119 | Mediocre |
| Comparative Example 7 | D-4 | CG-1X | HT-B | ET-1 | +699 | +125 | Mediocre |
| Comparative Example 8 | D-5 | CG-1X | HT-B | ET-4 | +700 | +122 | Mediocre |
| Comparative Example 9 | D-6 | CG-2Y | HT-B | ET-4 | +701 | +119 | Mediocre |
| Comparative Example 10 | D-7 | CG-1X | HT-C | ET-1 | +700 | +118 | Excellent |
| Comparative Example 11 | D-8 | CG-1X | HT-C | ET-4 | +700 | +116 | Excellent |
| Comparative Example 12 | D-9 | CG-2Y | HT-C | ET-4 | +701 | +113 | Excellent |

The multi-layer photosensitive members A-1-A-10 and the single-layer photosensitive members C-1-C-18 each contained the triphenylamine derivative 1 (specifically, any of the triphenylamine derivatives HT-1-HT-10) as a hole transport material. Therefore, these photosensitive members had small absolute values of residual potential ($V_L$) and were excellent in electric properties, as is clear from Tables 2 and 3.

The photosensitive layers of the multi-layer photosensitive members A-1 and A-2 and the single-layer photosensitive member C-1-C-6 each contained as a hole transport material, the triphenylamine derivative 1 represented by general formula (1-2) where m represents 2 and q represents 1 (specifically, the triphenylamine derivative HT-1 or HT-2). Therefore, these photosensitive members were excellent in electric properties and crystallization of the respective photosensitive layers was inhibited, as is clear from Tables 2 and 3.

By contrast, the respective photosensitive layers of the multi-layer photosensitive members B-1-B-3 and the single-layer photosensitive members D-1-D-9 did not contain the triphenylamine derivative 1 as a hole transport material. Therefore, these photosensitive members had large absolute values of residual potential ($V_L$) and were poor in electric properties, as is clear from Table 2 and 3.

The above evaluation results show that a photosensitive layer can be improved in electric properties when containing the triphenylamine derivative 1. The results also show that a photosensitive member including a photosensitive layer containing the triphenylamine derivative 1 was excellent in electric properties.

What is claimed is:

1. An electrophotographic photosensitive member comprising a conductive substrate and a photosensitive layer, wherein
the photosensitive layer contains at least a charge generating material and the triphenylamine derivative represented by general formula (1) shown below as a hole transport material:

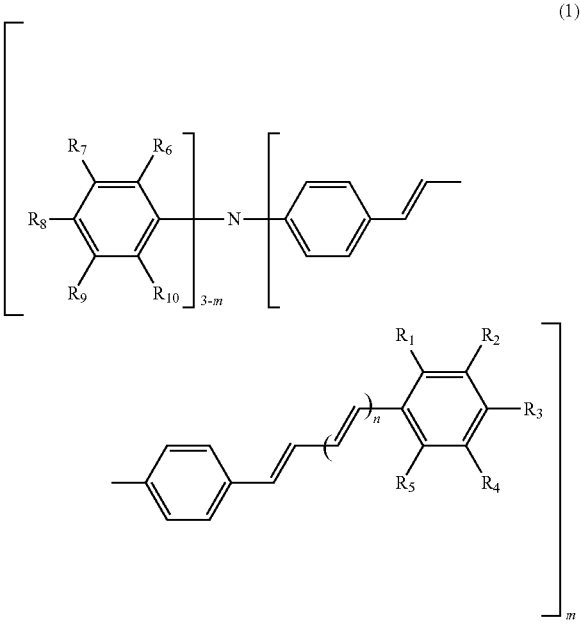

where, in the general formula (1), $R_1$, $R_2$, $R_3$, $R_4$, $R_5$, $R_6$, $R_7$, $R_8$, $R_9$, and $R_{10}$ each represent, independently of one another, a hydrogen atom, an optionally substituted alkyl group having a carbon number of at least 1 and no greater than 6, an optionally substituted alkoxy group having a carbon number of at least 1 and no greater than 6, an optionally substituted alkenyl group having a carbon number of at least 2 and no greater than 6, or an optionally substituted aryl group having a carbon number of at least 6 and no greater than 14, m represents 2, and n represents an integer of at least 0 and no greater than 2.

2. The electrophotographic photosensitive member according to claim 1, comprising, as the photosensitive layer:
a charge generating layer that contains the charge generating material and a charge transport layer that contains the hole transport material, or
a single-layer photosensitive layer that contains the charge generating material and the hole transport material, wherein
the charge generating material is a titanyl phthalocyanine having a crystal structure of Y-form.

3. The electrophotographic photosensitive member according to claim 1, wherein
the photosensitive layer is a single-layer photosensitive layer,
the single-layer photosensitive layer contains the charge generating material, the hole transport material, and an electron transport material, and
the electron transport material is a compound represented by following general formula (16):

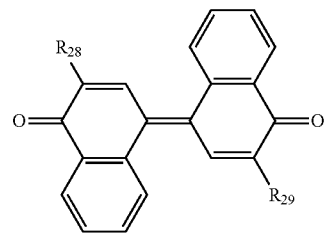

(16)

where in general formula (16), $R_{28}$ and $R_{29}$ each represent, independently of one another, a hydrogen atom, a cyano group, an optionally substituted alkyl group, an optionally substituted alkenyl group, an optionally substituted alkoxy group, an optionally substituted alkoxycarbonyl group, an optionally substituted aryl group, or an optionally substituted heterocyclic group.

* * * * *